United States Patent [19]

Kalman

[11] 3,972,320

[45] Aug. 3, 1976

[54] PATIENT MONITORING SYSTEM
[76] Inventor: Gabor Ujhelyi Kalman, P.O. Box 95, Farmington, Conn. 06032
[22] Filed: Aug. 12, 1974
[21] Appl. No.: 496,491

[52] U.S. Cl............................. 128/2.1 A; 128/2.05 P;
  128/2.06 F
[51] Int. Cl.²............................................ A61B 5/04
[58] Field of Search................... 128/2.05 R, 2.06 F, 128/2.1 A, 2.06 R, 2.1 R

[56] References Cited
UNITED STATES PATENTS

| | | | |
|---|---|---|---|
| 3,572,316 | 3/1971 | Vogelman et al................ | 128/2.1 A |
| 3,599,628 | 8/1971 | Abbenante et al.............. | 128/2.06 F |
| 3,639,907 | 2/1972 | Greatbatch...................... | 128/2.1 A |

*Primary Examiner*—William E. Kamm
*Attorney, Agent, or Firm*—Reising, Ethington, Barnard

[57] ABSTRACT

A monitoring system is disclosed for producing an alarm at a central station when a monitored condition at a monitor station deviates beyond a predetermined limit. The monitor system is especially adapted for monitoring a vital function of plural patients in a hospital so that a single attendant is alerted if any patient needs emergency treatment. The monitor unit is portable by the patient, suitably in the form of a wrist-unit, and a communications link, suitably by radio frequency transmission, is provided for one-way transmission from the monitor station to the central station. Each monitor station develops and processes data to determine whether the monitored condition has a value exceeding a predetermined limit; if so, an identification signal is transmitted to the central station to signify that an emergency exists at that monitor station. Each monitor station includes a programmed data processor to eliminate the need for transmitting variable data to the central station. Only fixed or stored data is transmitted for the purpose of identifying the monitor station. The processor electronics is suitably implemented in large scale integrated circuitry.

36 Claims, 15 Drawing Figures

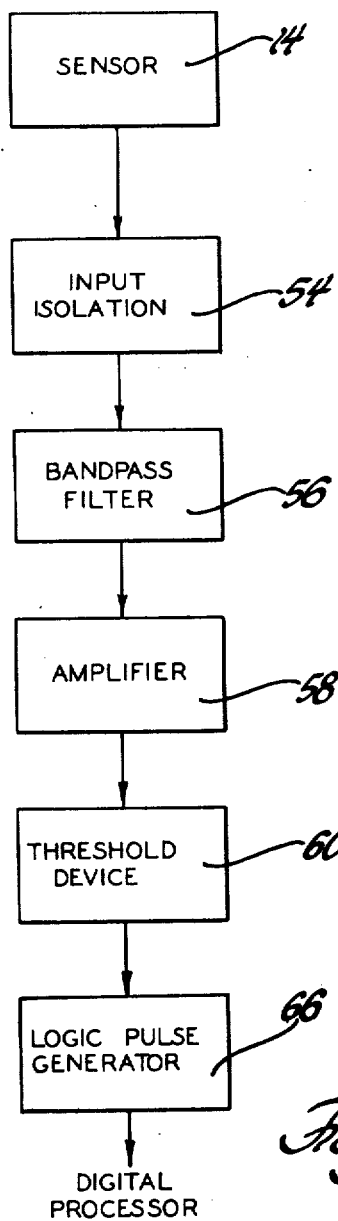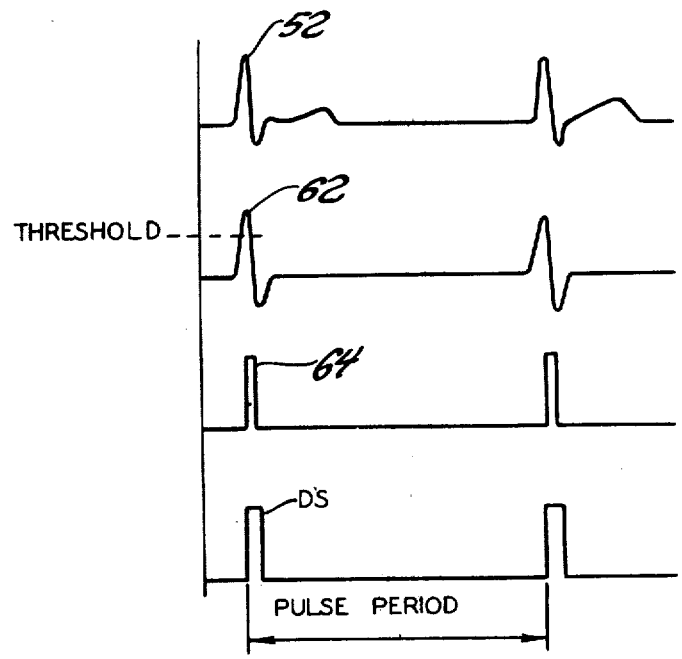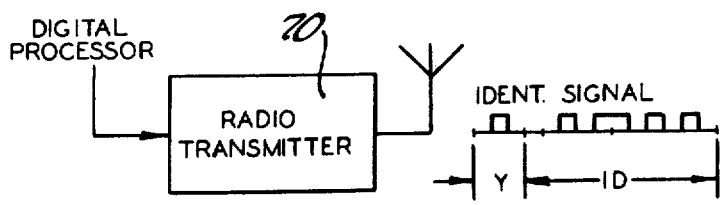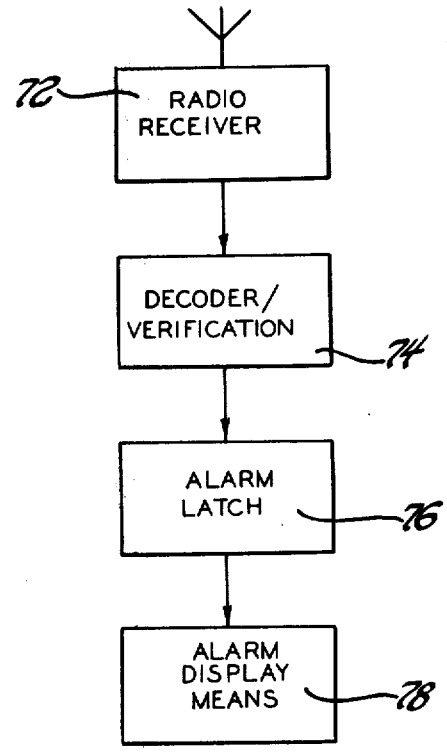

ALARM TRANSMISSION CYCLE

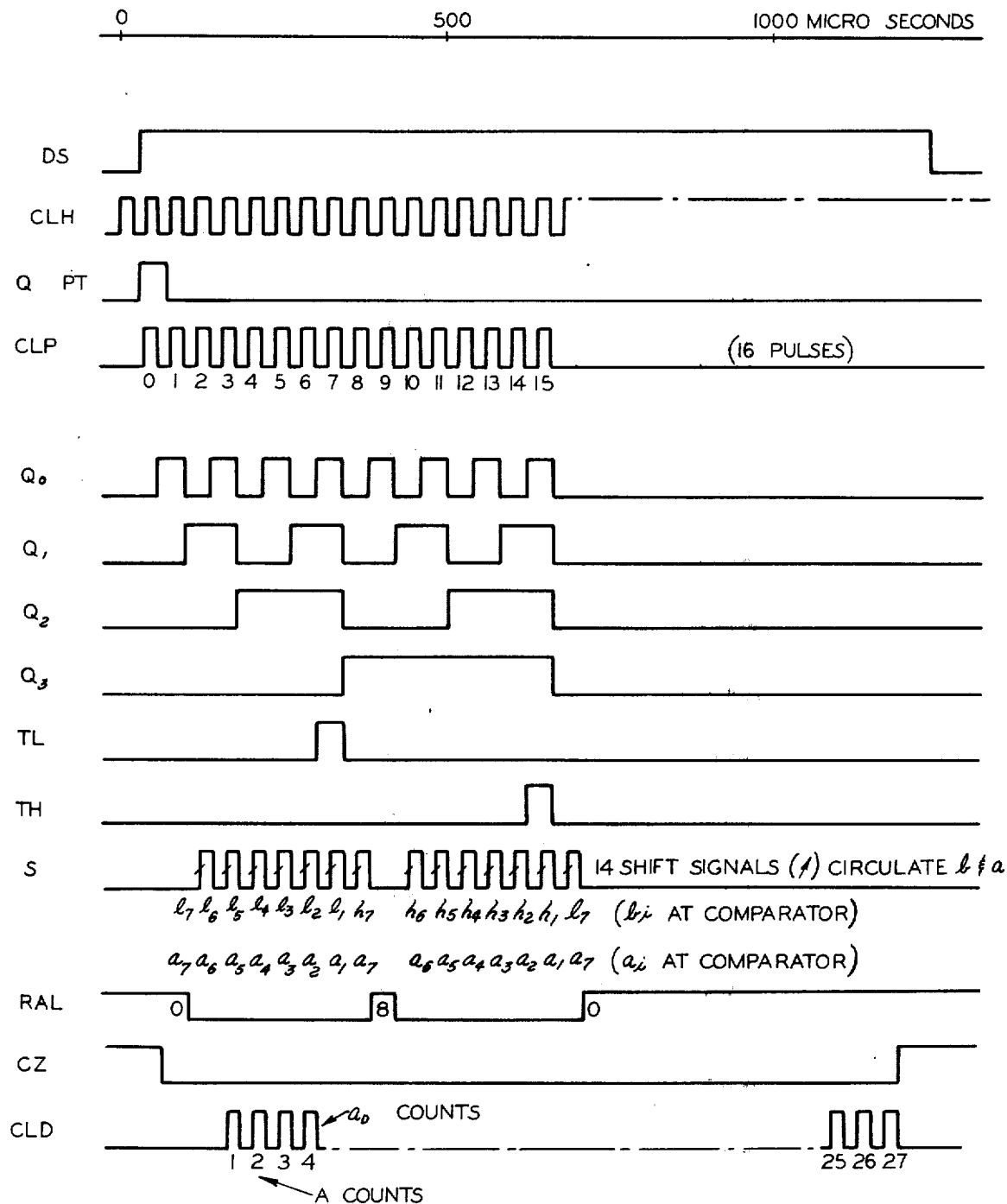

PATIENT MONITORING SYSTEM

FIELD OF THE INVENTION

This invention relates to monitoring systems and more particularly to a system which comprises a plurality of monitoring stations all of which may report to a single central station. In a particular application, this invention relates to a system for monitoring selected life functions of several persons such as patients in a hospital.

BACKGROUND OF THE INVENTION

In caring for patients in a hospital, such as those requiring intensive care, it is desired to provide continuous observations of one or more life functions of each patient; however, the common technique of providing such observation by trained nurses not only requires a large number of nurses but also actually falls short of continuous uninterrupted observation. It is therefore desired to provide a system for accomplishing the continuous observation of multiple patients by means of instrumentation and a single attendant who need not be highly trained.

Patient monitoring systems of various types have been proposed in the prior art. For the most part, these prior art systems may be characterized as telemetering systems wherein the patients or persons being monitored are fitted with one or more sensors which produce signals corresponding to a selected vital function of the person. The signals representing the vital function as detected by the sensors are then transmitted as data signals to a central processing station where the significance of the signals relative to the given patient is determined manually or by a data processing system. Patient monitoring systems of this type are described in the following U.S. Pat. Nos. Vogelman et al 3,572,316, Pacela et al 3,608,542, Buxton et al 3,646,606, and Greatbatch 3,639,907. The difficulty with these prior art systems is that they are very complex, especially at the central station in that they require computer or data processing equipment of relatively large capacity. Additionally, such prior art systems need a fairly sophisticated communication system between the patient monitoring stations and the central station. Because of the complexity and high cost, patient monitoring systems have not been used extensively and there remains a great need in providing multiple patient intensive care without exorbitant costs associated with presently known techniques.

SUMMARY OF THE INVENTION

According to this invention, a monitoring system, especially adapted for hospital patient monitoring, is provided which develops and processes data at the monitor station and transmits an identification signal to the central station only in case of an emergency. This is accomplished by assigning a monitor unit or station to each patient with a suitable identification code and providing a programmed data processor or computer within the monitor station so that the emergency status of the patient is decided at the monitor station. If an emergency exists, a transmitter at the monitor station is activated and transmits the station identification to the central station. The central station decodes the identification signal and produces an alarm display to invoke an emergency procedure for treatment of the patient in distress.

Further, in accordance with this invention, the monitor station is portable by the patient, preferably as a wrist-unit or as a pendant on a necklace. This is accomplished by implementing the processor electronics in microcircuits and minimizing the need for communication between the monitor station and the central station. Additionally new signal processing means have been developed to permit the processor to be implemented with a minimum number of stages while affording ample capacity in programming and computation.

A more complete understanding of this invention may be obtained from the detailed description that follows taken with the accompanying drawings in which:

FIG. 4 is a block diagram of the analog signal processing stages;

FIG. 5 is a waveform diagram of the heartbeat signal and logic signal;

FIG. 6 is a block diagram of the transmitter;

FIG. 7 is a block diagram of the central station;

Figure 12:
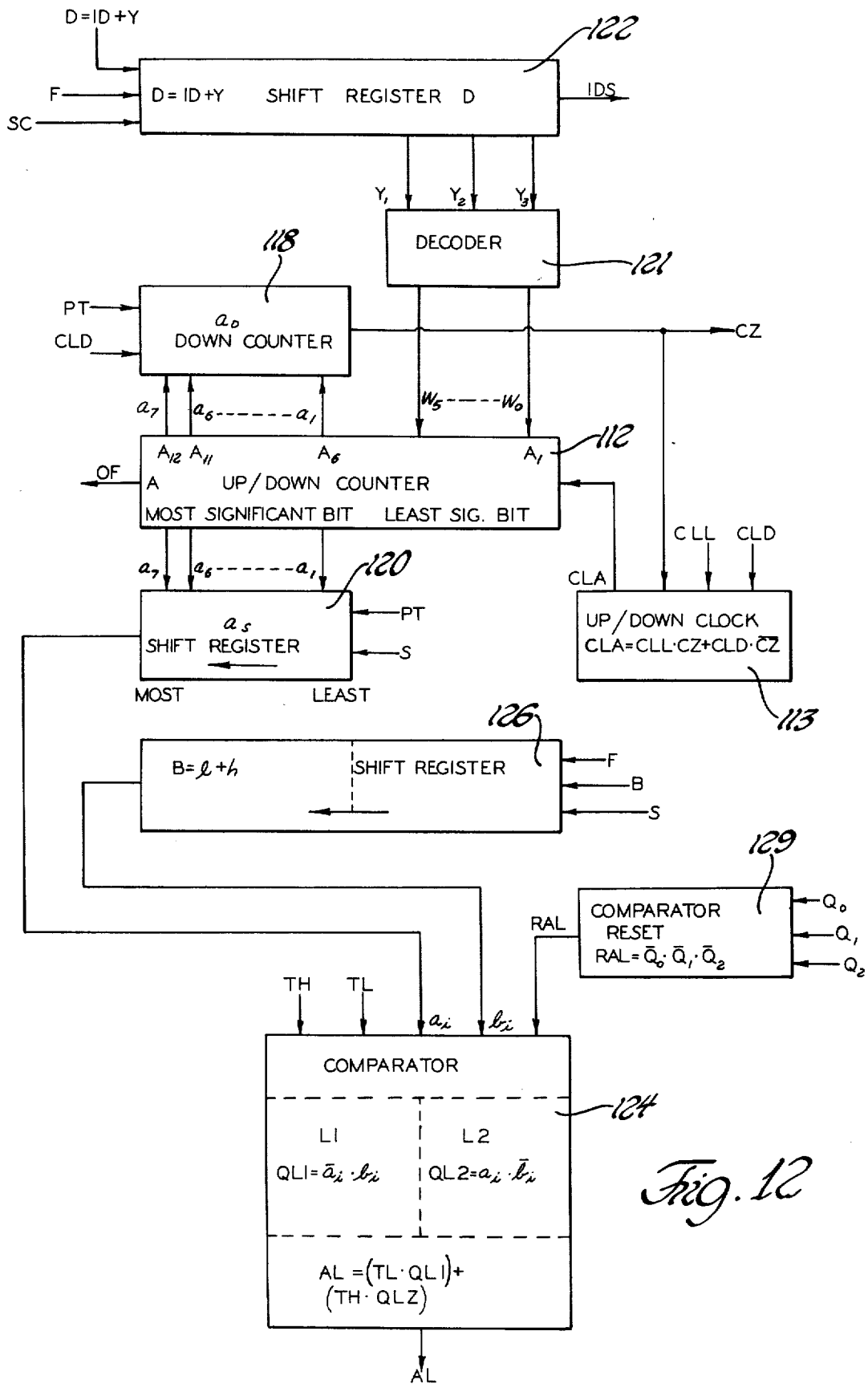
Figure 13:
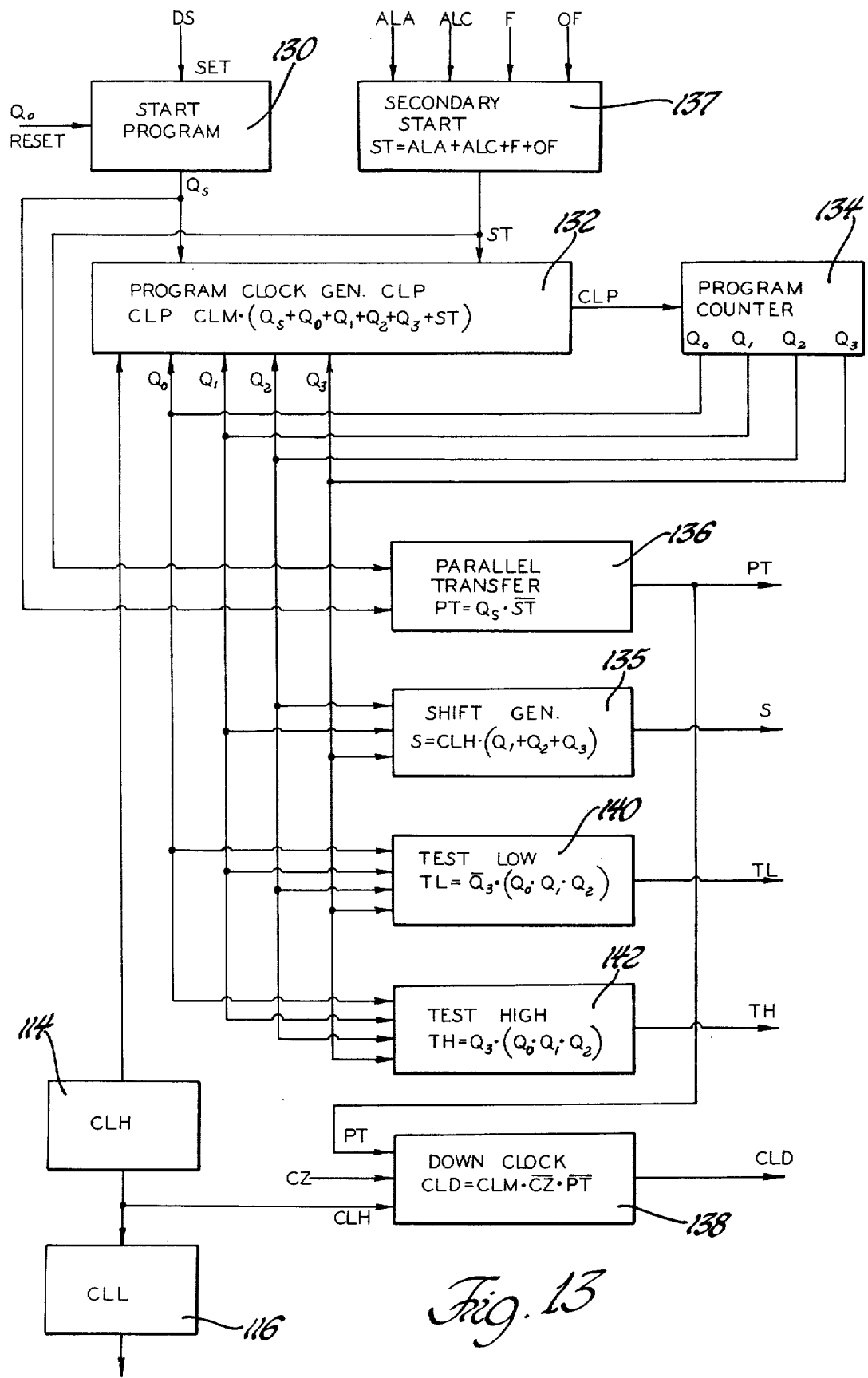
Figure 14:
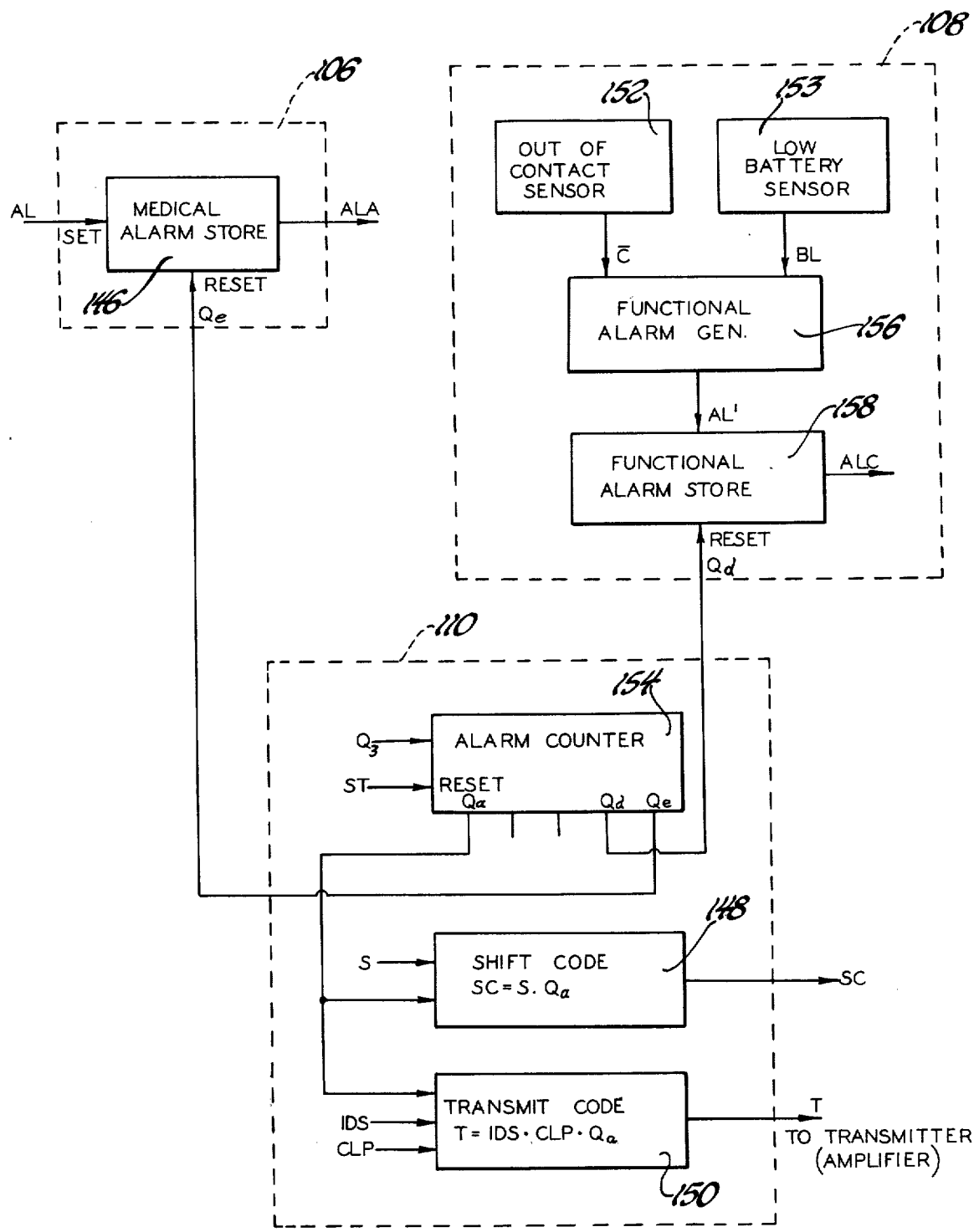

FIGS. 12, 13 and 14 taken together represent the digital processor of the monitor station; and FIG. 15 is a timing diagram pertaining to the computation cycle of the digital processor.

DETAILED DESCRIPTION

Referring now to the drawings, there is shown an illustrative embodiment of the invention in a patient monitoring system; in particular, the illustrative embodiment is a system for monitoring the pulse or heartbeat rate of multiple persons in a hospital or clinic. It will be appreciated as the description proceeds, that the invention is applicable to the monitoring of other life functions of persons or animals. Additionally, it will be seen that the invention is not limited in its use to the monitoring of life or vital functions; instead, it may be used in the monitoring of physical conditions at multiple stations, such as may be desired in industrial plants or in military applications and the like.

As alluded to above, the subject invention in the illustrative embodiment is adapted for continuous monitoring of a selected life function of one or more persons and reporting to a central station when a predetermined condition occurs. In the particular illustrative embodiment to be described, the invention is adapted for use in a hospital for monitoring the heartbeat rates of multiple patients. Each individual patient is supplied with a monitor station or remote unit which is suitably attached to the patient. The monitor station may be attached in various ways such as by a wrist band or as a pendant on a neck band; in the illustrative embodiment it takes the form of a wrist-mounted unit, in the manner of a wristwatch. Each monitor station is adapted to sense a selected condition relating to a life function of the person, develop data signals corresponding thereto, process the data signals and transmit an alarm to the central station in the event that the monitored condition reaches a predetermined value. The central station, which is attended by an operator, is effective upon receipt of a transmitted signal to produce a display or audible alarm which identifies the individual monitor station which originated the transmission.

Figure 1:
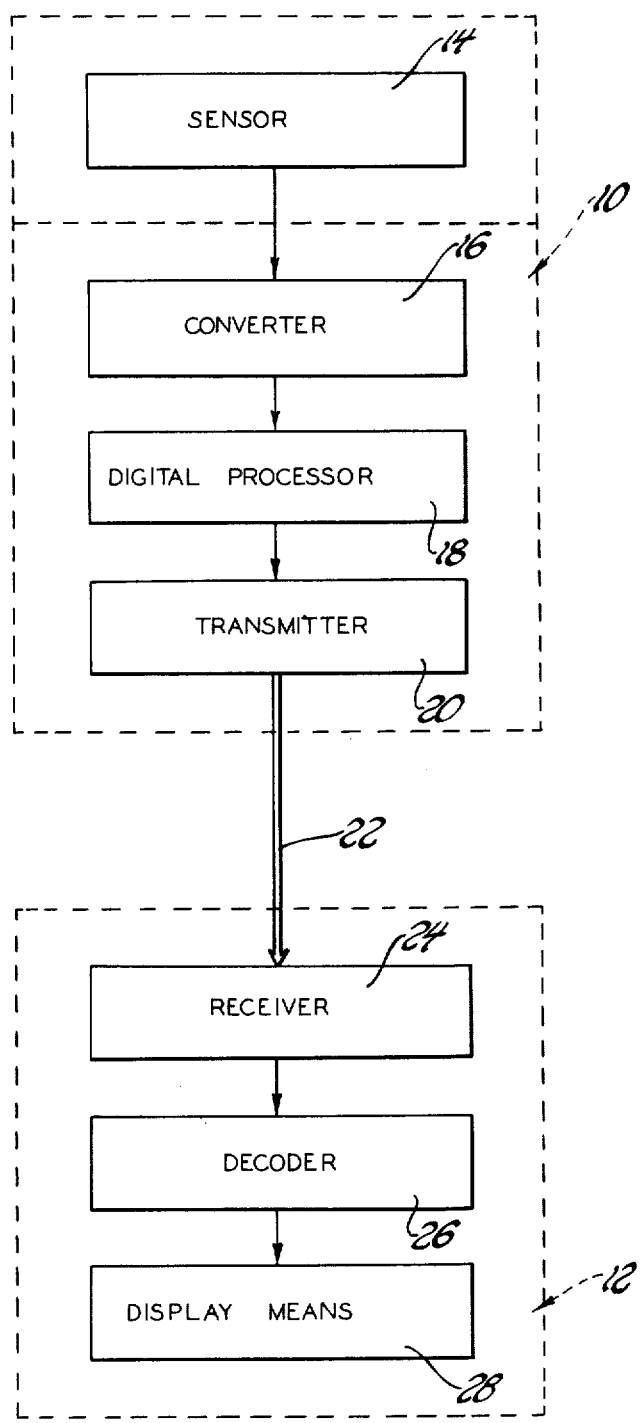
FIG. 1 is a block diagram of the monitor system.

FIG. 1 is a block diagram representation of the monitoring system including a monitoring station 10 and a central station 12. The monitoring station includes a sensor 14 which is adapted to produce a signal indicative of a physical condition; for example, the sensor 14 may be a transducer in the form of two electro-cardiograph electrodes, an acoustical transducer responsive to the pulse at a person's wrist, or a thermometer adapted to produce an electrical output signal corresponding to temperature. The sensor output signal, which is in the form of an electrical analog signal, is converted to logic signal form by an analog to logic level converter 16 and then applied to the input of a digital processor 18. The digital processor performs specified mathematical computations or other manipulations of the input data and, under certain circumstances, produces an output signal which is applied to a transmitter 20. A transmitting means including a transmitter 20 and a communications channel, such as a radio link indicated by the arrow 22, is adapted to send a coded signal to the central station 12. The central station comprises a signal receiver 24 which is capable of accepting transmitted signals through the communications link 22 from any one of a multiplicity of individual monitor units 10. The output of the receiver 24 is applied to a decoder 26 which is operative in response to the transmitted signal to produce an identification signal which is applied to the input of a display or alarm means 28 which is adapted to identify the transmitting monitor station to the operator attending the central station.

THE MONITOR STATION

Figure 2:
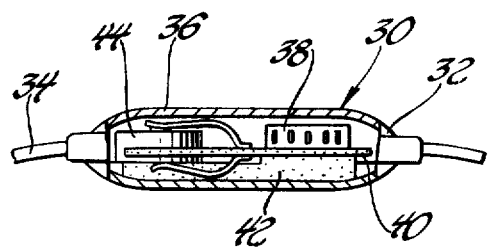
FIG. 2 is a side view with parts cut away of the monitor station in the form of a wrist-unit.
Figure 3:
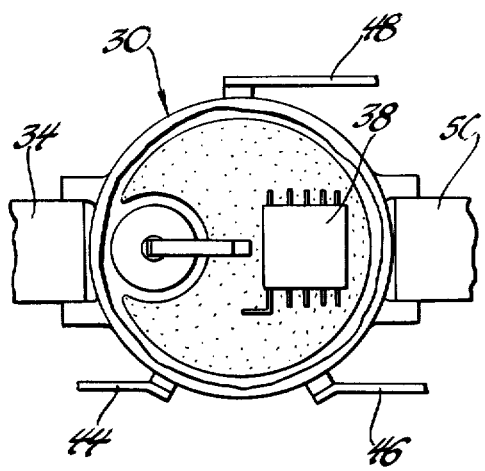
FIG. 3 is a plan view of the wrist unit.

An exemplary embodiment of the monitor station in the form of a remote unit 30 is shown in FIGS. 2 and 3. This remote unit comprises a case 32, preferably constructed of metal and hermetically sealed, which is fitted with a wrist strap 34 adapted to be fitted around a host person's wrist, as by a buckle, not shown. The case 32 includes a removable metal lid 36 to permit access to the interior of the case for servicing. An electronics package or assembly 38 is mounted upon a substrate 40 which in turn is supported upon a base member 42 inside the case. A battery 44 is connected by suitable electrical leads to conductors on the substrate 40 to supply electrical power to the electronics assembly. As will be described subsequently, the electronics assembly 38 takes the form of a large scale integrated circuit, preferably of the type known as complementary symmetry metal oxide semiconductor (CMOS) integrated circuits. This technique of circuit manufacture permits a vast number of transistors to be disposed within a very small volume. The CMOS integrated circuit exhibits an exceedingly small power drain on the power supply. The electronics assembly 38 comprises the analog to logic level converter 16, the digital processor 18, and the transmitter 20 which were described with reference to FIG. 1. An electrode 44 and an electrode 46, both of the electro-cardiograph type, are mounted upon the case 32 exteriorly thereof for electrical connection with the body of the host person at selected points. The electrodes are adapted to produce an electrical signal indicative of the heartbeat of the host person in a well-known manner. The electrodes are insulated from and extend through the wall of the case 36 into electrical connection with the electronics assembly 38. The electrodes 44 and 46 constitute the sensor 14 which was referred to in connection with FIG. 1. The remote unit 30 is also provided with an antenna lead 48 which is insulated from the case and extends through the wall thereof from the electronics assembly 38 to a metal wrist band 50 which constitutes a transmitting antenna and comprises a portion of the transmitter 20.

The electronics system preferably includes sensor signal processing stages for producing a logic level signal as illustrated in FIG. 4. The sensor 14, in the form of the electrodes 44 and 46, detects an electrical signal 52, such as that shown graphically in FIG. 5. This electrical signal has a peak amplitude of a few millivolts and each of the impulses corresponds to a heartbeat of the host person. Each impulse is characterized by an initial, high amplitude positive pulse followed by a negative pulse of lesser amplitude which in turn is followed by a trailing low amplitude positive pulse. Each impulse which corresponds to a heartbeat typically has a duration of around twenty milliseconds. The interval between heartbeat impulses typically varies from about ½ second to about 2 seconds.

The signal received by the sensor 14 is applied through isolation means 54 to prevent accidentally applied or spurious excessive voltages from reaching the electronic devices and to prevent the application of electronic system signals to the host person. The sensor signal is also applied through a bandpass filter 56 to exclude noise which might accompany the signal. The output of the filter is applied to the input of an amplifier 58 to increase the signal strength to a workable level. The output of the amplifier is applied to a threshold device 60 which is adapted to recognize significant signal characteristics, such as amplitude or time period. The filtered and amplified signal 62 is shown in FIG. 5. The threshhold device 60 is of the amplitude responsive type and as shown in FIG. 5, produces a rectangular pulse 64 in response to the signal 62 exceeding the threshhold level. It is noted that the amplifier may be of fixed gain followed by a variable threshhold device or, alternatively, a variable gain amplifier may be followed by a fixed threshhold device. The output of the threshhold device 60 is applied to a logic pulse generator 66 which produces a constant amplitude fixed duration logic level pulse DS, as shown in FIG. 5, corresponding to each pulse 64. The threshhold device 60 and pulse generator 66 correspond to the analog to logic level converter 16 referred to in connection with FIG. 1. The pulse DS has a duration of about 1 millisecond and, as indicated in FIG. 5, has a pulse period or time interval between pulses equal to the interval between successive heartbeats which typically may range from ½ to 2 seconds.

As described with reference to FIG. 1, the logic pulses DS are applied to the digital processor 18 for such computation or manipulation as may be required to determine whether an alarm or emergency signal should be transmitted to the central station. A typical example of the data processing which is performed by the processor 18 in the monitor station will now be described. (A detailed description of the processor itself will be given subsequently.) In the illustrative embodiment, the life function being monitored is the heartbeat rate of the host person wearing the monitor station in the form of the remote unit of FIGS. 2 and 3.

The data processing function will be described with reference to a selected patient (host person) in a hospital environment. It will be assumed that the patient's physician has determined that the patient's heartbeat rate should be monitored continuously and that the patient's condition is such that he should be attended to immediately in the event that his heartbeat rate on a time average basis, drops below 40 beats per minute or if it exceeds 120 beats per minute. Further, the physician specifies that the heartbeat rate should be determined as a time average with the average being calculated for a base period corresponding to eight successive heartbeats of the patient. If the heartbeat rate of the patient should be outside the low and high limits specified by the physician, the remote unit is to transmit a medical emergency signal which will summon medical help.

In addition to the patient monitoring function specified by the physician, the remote unit is adapted to perform a self-checking function and report the occurrence of a malfunction so that its capability in monitoring the condition of a patient will be known at all times. For this purpose, one or more self-checking means are provided within the remote unit and signals are developed or supplied to the processor. Such signals are utilized by the processor to determine whether a malfunction exists and, if so, a malfunction emergency signal is transmitted to the central station.

As described above, the monitor station (wrist unit) is independently capable of ascertaining whether the patient's condition (heartbeat rate) is inside or is outside the limits specified by the physician. This ascertainment is made at the monitor station by digital data processing which comprises the production of a signal quantity which is the function of two or more variables and comparison thereof with one or more reference quantities. The performance of the data processing at the monitor station eliminates the need for communication with the central station except in the case of an emergency situation. In particular, a transmission need be made regarding the patient condition only if and when the condition is outside the specified limits; then, it is only necessary to transmit an identification code word or signal which identifies the monitor station which produces the alarm so that the attendant at the central station can dispatch medical help to the patient in distress. Additionally, the monitor station will send an emergency signal transmission when the self-checking means of the monitor station signifies that a malfunction exists in the monitor station. In this case, only a signal identifying the monitor station with the malfunction need be transmitted so that the attendant at the central station knows that the monitor station cannot be relied upon until the malfunction is corrected. In the case of the medical alarm, i.e., with the heartbeat rate outside the specified limits, the emergency signal T, which is a burst of identification code words, is transmitted repeatedly for an indefinite number of times. Preferably, the emergency signal T is transmitted repeatedly until medical aid reaches the patient in distress or until the battery is run down and the remote unit is unable to continue transmission. For functional alarm where a malfunction occurs in the monitor station the emergency signal T is transmitted a definite number of times, preferably four times, and then the transmission is terminated.

This arrangement, including data processing at the monitor station and transmission only of a identification signal, permits simplified signalling with a common signal channel for all monitor stations. Since no raw or intermediate data is transmitted to the central station, the communication link is passive until an emergency occurs at one of the monitor stations. There is no problem of bandwidth requirement for the communication link and there is no problem of crosstalk among the several transmitting stations. If simultaneous emergency transmissions occur the overlap will be limited (as discussed further below) so both stations can be identified.

A radio communication link between a monitor station and the central station is shown in FIG. 6 and FIG. 7. The radio transmitter 70 is a pulse code modulated transmitter with a carrier wave at an assigned fixed frequency. The carrier frequency is the same for all the monitor stations which communicate with the same central station. The digital processor 18, as described with reference to FIG. 1, is operative to control the transmission by the transmitter 70. When an alarm signal is developed by the processor, the transmitter 70 is turned on and the modulator thereof receives the identification code word in binary form in a serial feed of the code bits. The identification code word is supplied to the transmitter a definite number of times, e.g. eight times, in the case of a functional alarm signal from the processor and then the transmitter is turned off. In the case of a medical alarm signal being developed by the processor, the transmitter is turned on and the identification code word is fed to the modulator a larger number of times, for example, sixteen times, followed by a delay interval of, for example, 4 seconds duration. The burst or series of identification code words followed by the delay interval is repeatedly transmitted an indefinite number of times. Each of the identification code words is a binary word, which includes an identifier code ID and programming code Y. In the preferred embodiment, the identification code word is a 14 bit word with eleven bits allotted to the identifier code which is assigned to the particular monitor station and which distinguishes it from other monitor stations. Some of the eleven bits of the identifier code may be used for an error checking code. The remaining three bits in the identification code word are allotted to the programming code Y for use by the processor; in the illustrative embodiment, this programming code Y specifies the number of heartbeats which is to be used as the basis for determining the average heartbeat rate. A typical identification code word or signal, as emitted by the transmitter 70, is illustrated in FIG. 6 showing the allocation of bits for the identifier code ID and the programming code Y.

THE CENTRAL STATION

The central station for the monitoring system utilizing a radio communication link is shown in FIG. 7. A radio receiver 72 is tuned to the radio frequency carrier wave assigned to the monitor system. The emergency signal T is received and demodulated by the receiver 72 and the resulting identification code word is applied to the input of a decoder 74 which converts the code word into a digital signal. The decoder includes a code signal verification means wherein the received alarm code in digital form is compared with the list of alarm codes which have been assigned to monitor stations in the system. The many repetitions of the transmitted code word are compared with each other to verify the identification of the monitor station sending the alarm signal.

The decoder 74 converts the binary code word into a corresponding decoded identifier word such as a decimal number assigned to the monitor station. Alternatively, the decoder may translate the binary code word into the patient's name. The decoder 74 produces an output signal which represents the decoded identifier word. The output signal from the decoder is applied to the input of a latch circuit 76 which stores the decoded identifier word which corresponds to the monitor station represented by the identification code word. The latch circuit 76 is connected with an annunciator preferably in the form of a display means 78 which produces illuminated characters corresponding to the number or name of the monitor station which transmitted the alarm signal. The display 78 is disposed within view of the central station attendant and may be accompanied by an audible alarm to draw attention to the display means.

The aforementioned display means may be used as a main display means to signify a current or existing alarm in conjunction with plural auxiliary display means to signify previous alarms. The main display means, of relatively large size, receives the number or name of the monitor station directly from the latch circuit 76 immediately upon receipt of the emergency signal. The number or name is held in the main display means until the attendant acknowledges receipt of the alarm by operating a switch. This causes the number or name to be transferred to an auxiliary display means and the main display means to be cleared. The number or name is held in the auxiliary display means until manually cancelled when the emergency is over.

LOADING AND TESTING OF MONITOR STATION

Before any of the monitor stations is put into use for monitoring the heartbeat rate of a given patient, it must be provided with certain data which is relevant to the patient to be monitored. The supply, or inputting of data, also referred to as programming, is accomplished by means shown in FIG. 8. In general, there are two types of data to be loaded into the monitor station. One type is the identifier code which identifies the particular monitor station and, hence, the patient to which it is assigned. The other type of input data relates to parameters of the monitoring function; in particular, for the monitoring of the heartbeat rate, the acceptable limits of the heartbeat rate must be specified. While these limits may be specified in various ways, e.g., as beats per minute or as pulse period, it is desirable to use an average value taken over a specified time period. For example, the attending physician of a given patient may specify that an emergency signal must be sent if the patient's heartbeat rate falls below an average of 40 beats per minute or if it rises above an average of 120 beats per minute, the average being taken over the time period of the last 16 beats. This time period for deriving the average heartbeat rate, referred to herein as the averaging period, may be selected from a wide range of values.

Figure 8:
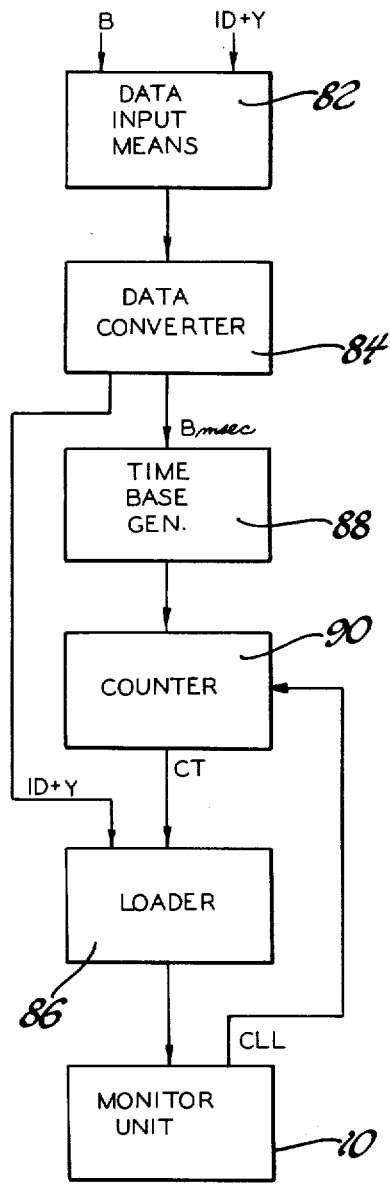
FIG. 8 is a block diagram of the programming means for the monitor station.

Referring now to FIG. 8, the input data for programming the monitor station is supplied through a manually controlled input means 82, preferably in the form of a keyboard. The identification code word ID+Y for the monitor station is fed serially by bit into a memory section, such as a shift register, of the integrated circuit chip. The programming word Y is comprised of three bits which specify the value of the averaging period as 1, 2, 4, 8, 16, or 32 heartbeat periods. Also, the data input means 82 accepts the specification of the lower and upper limits of heartbeat rate. This input is in the form of a data word B which is comprised of fourteen binary bits with the lower limit being expressed in the first 7 bits and the upper limit being expressed in the last 7 bits. The data input for the data word B is suitably expressed in heartbeats per minute at the keyboard.

The output of the data input means 82 is applied to a data converter 84 which is operative to convert the input data to the format required by the processor. The ID code and the programming code Y are applied directly from the converter 84 to a loader 86. The loader 86 supplies the data word ID+Y in serial fashion to the assigned register in the processor.

The data word B, which represents the lower and upper limits of the heartbeat rate, may also be supplied directly to the loader 86 which is operable to feed the data word B in serial fashion into the assigned storage register of the processor. However, for the purpose of providing a high degree of accuracy in the timing function of the monitor station, additional means are provided for loading the monitor station with the data word B. Since the heartbeat rate is of critical importance in the monitoring function it must be measured accurately at the monitor station; while this could be accomplished with a precision local oscillator or clock in the monitor station, such means are costly in terms of components and space requirements. Instead of a precision clock, an oscillator having a relatively wide frequency tolerance is provided and the output thereof is compared with a precision time base generator prior to loading the monitor station with the data word B. As shown in FIG. 8, the data word B is supplied to the data converter 84 and the output thereof is applied to a time base generator 88. The first 7 bits of the word B specifies the lower limit of the heartbeat rate in beats per minute which, or course, corresponds to a heartbeat period which is expressed in a definite number of milliseconds. The data converter applies a signal to the time base generator indicative of the heartbeat period and the time base generator produces an output signal of the specified duration. This time base signal is applied to the input of a counter 90 to enable the counter for the duration of the time base signal. During this loading process, the clock oscillator is running in the monitor station 10 and the low frequency clock signal CLL is applied to the count input of the counter 90. In the illustrative embodiment, the low frequency clock signal has a nominal frequency of 80 Hz and typically the frequency of a given monitor station will be different from the nominal frequency by as much as 10%. During the time base signal from the generator 88, the counter 90 will accumulate a count equal to the number of low frequency clock pulses which occur during the specified low limit period. For example, it may be assumed that the low frequency clock has a nominal frequency of 80 Hz and that the low limit specified by the attending physician for the given patient is to be 48 heartbeats per minute, which is equivalent to a pulse period of 1.25 seconds. Accordingly, the time base generator 80 provides a timing pulse of 1.25 seconds duration to a high degree of accuracy. During this timing pulse the counter 90 reaches a count of 110 which means that the low frequency clock is 10% fast and the low limit to be established in the monitor station is a low frequency clock pulse count of 110. The same means and technique are utilized for establishing the high limit for the heartbeat rate in the monitor station. The output of the counter 90 is applied to the loader 86 which feeds a low limit code and a high limit code into an assigned shift register in the processor.

After the monitor station is loaded with the required data as just described, it is desirable to test the monitor station for proper functioning before it is put into use on the assigned patient. This testing is performed in a manner indicated by the process flow diagram of FIG. 9. The monitor station 10 to be tested is connected with a body signal simulator 92 which, in the illustrative embodiment, supplies simulated electrical heartbeat signals to the two electrodes of the monitor station. The simulated heartbeat signals are supplied at various heartbeat rates under the control of a variable signal generator 94. A program control unit 96 applies a control signal to the variable signal generator 94 to cause the signal variation and hence the simulated heartbeat signals to vary in accordance with a predetermined program. The monitor station 10 responds to the simulated heartbeat signals and, if it is functioning properly, it will transmit the medical alarm in the event the heartbeat rate falls outside the limits and it will transmit a functional alarm in the event of a malfunction in the monitor station. If the simulated heartbeat rate remains within the lower and upper limits and if there is no malfunction, there will be no transmission from the monitor station. The central station 12 responds to any transmitted medical alarm or functional alarm and the output of the latch circuit which indicates receipt of one or the other of such alarms is applied to the program control unit. The program control unit 96 performs a comparison between the actual output from the monitor station and an output which should have been produced, if any, by the simulated heartbeat signal. If the actual output and the programmed output are the same, the monitor station is operating properly, and the program control unit produces an output signal indicative of proper operation. This output signal is applied to an indicator 98 which indicates that the monitor station has passed the test program.

GENERAL DESCRIPTION OF THE PROCESSOR

Figure 10:
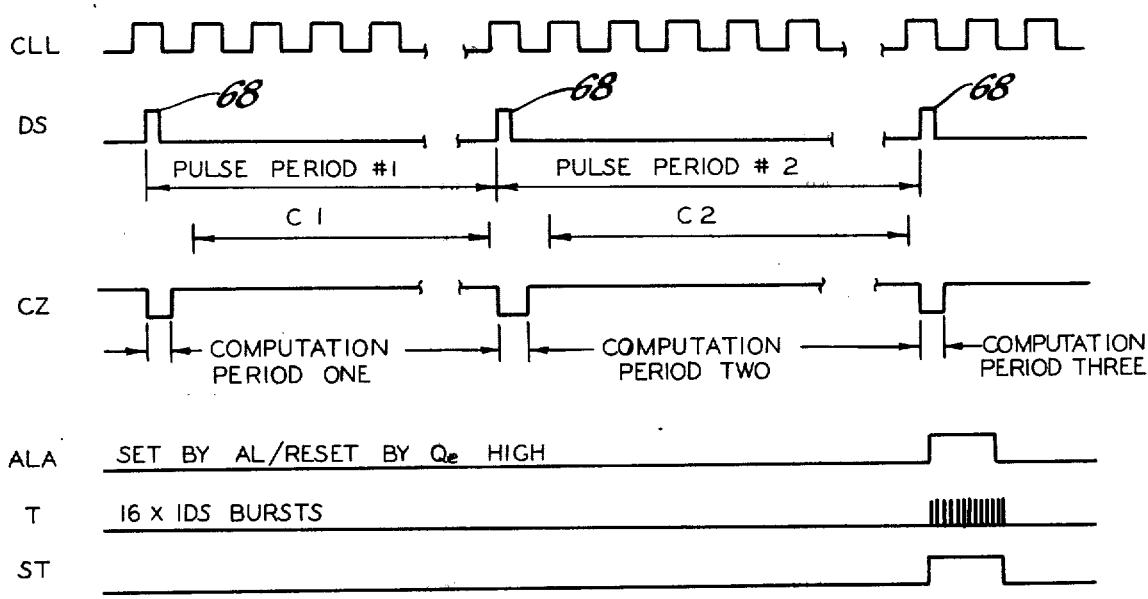
FIGS. 10 and 11 are timing diagrams.

Before describing the details of the processor in the monitor station, it will be helpful to consider the timing diagram of FIG. 10. As discussed above, the analog to logic level converter 16 produces a logic signal DS comprising a series of pulses 68, each of which corresponds to a heartbeat signal produced by the sensor 14. The logic pulses 68 have a pulse duration of about one millisecond and the pulses are separated by the pulse period which may vary from about ½ second up to about 2 seconds. As indicated in FIG. 10, on the graphical representation of the logic signal CZ, the computation is performed by the processor within a period of about 2 milliseconds beginning with leading edge of the pulse 68. In other words, the computation is performed intermittently, i.e., at spaced time intervals at the end of each pulse period. The computation period is less than 2 milliseconds while the pulse period is hundreds of times longer. However, it is noted that a computation is performed immediately upon receipt of an additional increment of data, namely, after each measurement of the heartbeat rate derived from the latest heartbeat.

With further reference to FIG. 10, it is noted that the heartbeat rate is continuously measured by counting the number of low frequency clock pulses CLL which occur in each of the pulse periods. As indicated in FIG. 10, each clock pulse has a duration which is several times greater than the duration of the logic pulses 68. For example, with a low frequency clock rate of 80 Hz the clock pulse period is 12.5 milliseconds and the pulse duration may be about 6 milliseconds. In the example represented by FIG. 10, the pulse period 1 is of such time duration that the counter for the low frequency clock pulses CLL accumulates a count of C1; during the succeeding shorter pulse period 2 the accumulated count is C2.

Figure 11:
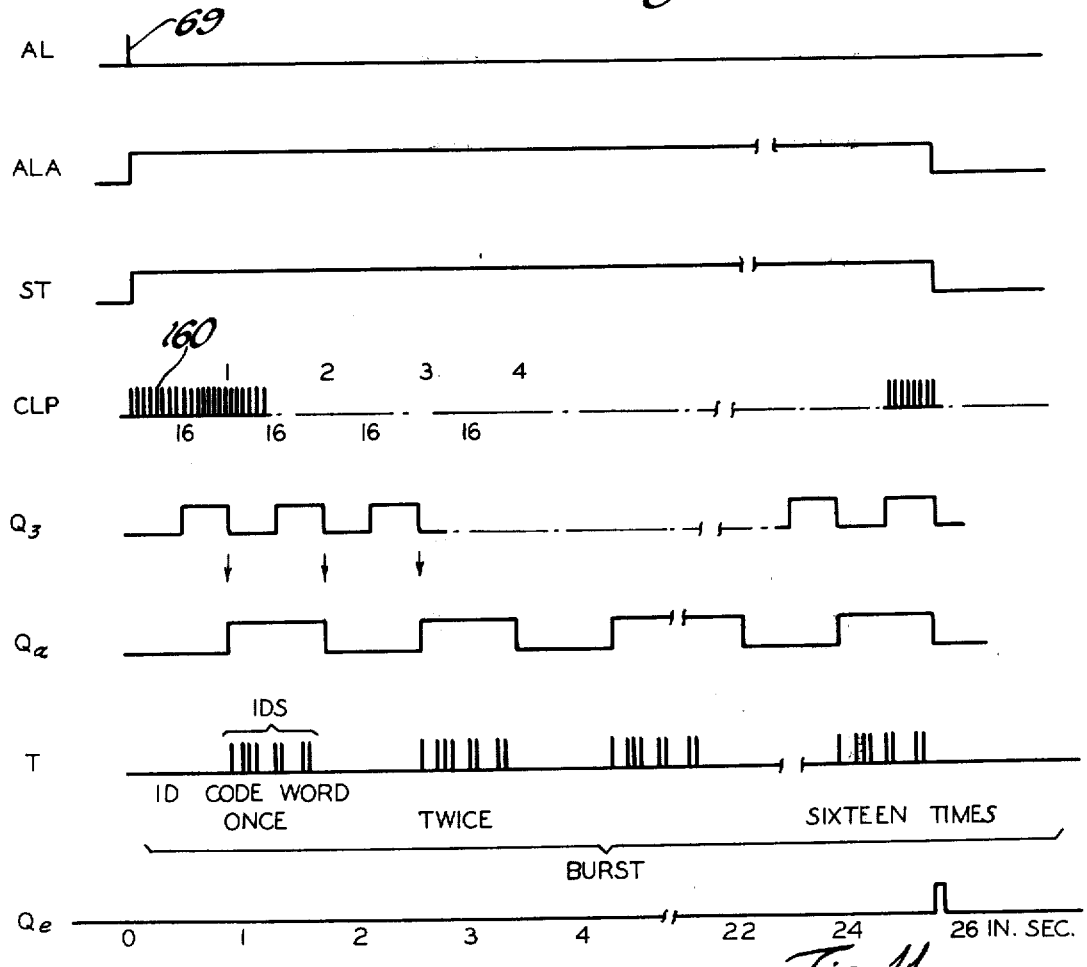

During the computation period, by means to be described presently, the processor computes the average number of low frequency clock pulses per pulse period over a specified number of periods, for example eight pulse periods. The processor, during the computation period, also compares the computed average number of low frequency clock pulses with the specified lower and upper limits, expressed in number of clock pulses, and if it is outside the limits, a medical alarm signal ALA is generated. As depicted in FIG. 10, an alarm signal ALA is generated at the end of pulse period 2 during which the count C2 of the low frequency clock signal CLL dropped significantly with respect to the previous pulse periods. This would indicate a significant increase in the heartbeat rate and, presumably, for the example given, the average count during the computation period 2 decreased below the lower limit. This would cause the alarm signal ALA to be generated. Upon the occurrence of an alarm signal, the processor during the computation period causes an emergency signal T to be sent from the monitor station to the central station. This emergency signal T, as indicated in FIG. 10, for a medical alarm, has a time duration which is long relative to the computation period. In the illustrative embodiment, as mentioned above, an emergency signal comprises a series of successive transmissions of the identification code word. This series of the identification code word, termed a burst, is followed by a delay interval before another burst is transmitted and this pattern is repeated indefinitely. As shown in FIG. 11, each burst is comprised of 16 identification code words and, as discussed above, each identification code word comprise 14 bits. Each burst, as shown, is followed by a delay of 4 seconds or more before the succeeding burst is transmitted.

In the event of a malfunction in the processor, as will be discussed presently, a functional alarm signal AL' is generated by the processor during the computation period and this signal is effective to initiate transmission of a functional alarm. The functional alarm comprises a single burst which is made up of a series of four identification code words. This transmission is not repeated between logic pulses 68; however, if the malfunction persists, then upon the occurrence of the succeeding logic pulse 68, the processor will cause the same malfunction alarm signal to be transmitted again.

DETAILED DESCRIPTION OF THE PROCESSOR

For a description of the processor, reference is made to FIGS. 12, 13 and 14 which, taken together, disclose the processor in block diagram. In general, the processor comprises a timing and control section (shown in FIG. 13), a computation section (shown in FIG. 12) and, as shown in FIG. 14, a medical alarm section 106, a function alarm section 108, and an alarm transmitter and control section 110. The computation section comprises an up/down counter 112 which is used for accumulating the count of low-frequency clock pulses which occur during a specified number of heartbeats or pulse periods. The counter 112 is provided with a count input terminal which receives a clock input signal CLA from an up/down clock 113. This clock has an input which receives a low frequency clock signal CLL and a high frequency clock signal CLD from the timing and control section 102 which will be described subsequently. Additionally, the clock 113 receives a count zero signal CZ from a preset down counter 118 in the computation section. The up/down clock 113 combines the input signals to produce an output clock signal CLA of either high frequency or low frequency, in accordance with the following logic equation:

$$CLA = CZ \cdot CLL + \overline{CZ} \cdot CLD \qquad (1)$$

The up/down counter 112 comprises bit positions A1 through A12. Positions A6 through A12 hold the existing count in binary form and positions A1 through A5 hold the data word W which will be discussed below. The up/down counter 112 is provided with parallel readout terminals corresponding to the respective bit positions A6 through A12. These parallel output terminals are connected with the down counter 118 and with a shift register 120 to enable parallel entry into the down counter and the register of the bits registered in the up/down counter. The up/down counter is utilized to obtain an average of the number of low frequency clock pulses received over a specified number of DS pulse periods. This is done by performing a division operation in binary form by effectively shifting bits of the dividend toward the least significant bit position by a numer of bit positions corresponding to the divisor. In the up/down counter 112 the dividend is the total existing count represented by the bits in bit positions A6 through A12; the divisor is supplied to the up/down counter through input terminals which receive the data word W from a decoder 121 which receives the programming code Y from a shift register 122. As discussed above, the programming code Y is a part of the identification code word ID+Y, where ID is the identifier code of eleven bits. The programming code Y is of three bits and specifies the number of heartbeats which is to be used as the basis for determining the average heartbeat rate. The decoder 121 produces the output data word W which is comprised of 6 bits in bit positions W0 through W5. The up/down counter is provided with parallel input terminals corresponding to bit positions A1 through A5. These input terminals are connected to respective output terminals of the decoder 121. In the data word W only one of the bits will be a binary 1 and its bit position specifies the value of the divisor which is 1, 2, 4, 8, 16, or 32 when the binary 1 is at bit positions W0 through W5 respectively. In the illustrative embodiment, the bit W3 is a binary 1 and hence the up/down counter is set to divide by 4; this division is accomplished by omitting the three least significant bits of the total existing count to obtain the quotient which is the average count. This average count is readout and is transferred to the down counter 118 and the shift register 120. The average count is transferred in parallel fashion to the down counter 118 and the shift register 120 in response to a parallel transfer signal PT which is applied to the counter 118 and register 120. This effects a transfer to the $a_1$ through $a_7$ bit positions according to the following relationship:

$$a_i = A(i + 5)$$

where $i$ = any integer from 1 to 7 \qquad (2)

Accordingly, the parallel transfer causes the bit in position A6 to be transferred to bit position $a_1$, and so on. The up-down counter 112 has an overflow output terminal which produces a signal OF when the counter is full and therefore unable to register any further count. The down counter 118, as mentioned above, is adapted to receive by parallel entry the latest average count of low frequency clock pulses which occur during a pulse period. The down counter has preset input terminals which receive the average count represented by the bits in bit positions $a_1$ through $a_7$ and the counter 118 is conditioned to accept this entry by a parallel transfer signal PT applied to an enable terminal. The down counter 118 also has a count input terminal which receives a clock signal CLD from the timing and control section 102. The down counter has an output terminal which produces a count zero signal CZ when the number of down clock pulses applied to the counter is equal to the preset count.

The shift register 120 is adapted for parallel input through a set of input terminals which receive the average count in the form of the bits in bit positions $a_1$ through $a_7$. The shift register has an enable input which receives the parallel transfer signal PT which conditions the register for receipt of the average count. The shift register 120 is adapted for serial output and is provided with a shift input terminal which receives a shift signal S from the timing and control section 102. The output terminal of the register 120 produces a signal ai (which is taken from bit position $a_7$) which in time sequence, as a serial output, becomes equal to each successive bit in the register, under the control of the shift signal. The register 120, as just described, converts the parallel input to a serial output and presents, in a bit by bit fashion, the average count which is held in the up/down counter 112 to a comparator 124.

The average count, during each computation period, is to be compared with the specified lower and upper limits for the average count. A shift register 126 of the serial input-serial output type is provided to hold the lower and upper limits of the average count. This register has a data input terminal which receives an input signal B which, in binary form, represents the lower and upper limits. As discussed above, the data signal B is loaded into the register 126 during the programming of the monitor station. The register includes an enable terminal which receives a feed signal F which conditions the register for the acceptance of the data signal B. The register 126 is loaded with two data words, namely, the lower limit of the average count which is represented by the first seven bits and the upper limit of the average count which is represented by the last seven bits of the data signal B. The lower limit data word is loaded into bit position $l_1$ through $l_7$ in the register and the upper limit data word is loaded into bit positions $h_1$ through $h_7$ in the register. The bits of each word are arranged in descending order of significance. The register 126 has a serial output terminal and the output signal $b_i$, which is taken from bit position $l_7$. The serial output signal $b_i$, in time sequence, becomes equal to each successive bit in the register, under control of the shift signal S. A shift input terminal of the register receives the shift signal S from the timing and control section 102. The output of the register 126 is presented bit by bit to the comparator 124.

The comparator 124 is a bit by bit comparator and has two input terminals which, as mentioned above, receive, respectively, the signal $a_i$ from the shift register 120 and the signal $b_i$ from the shift register 126. The comparator 124 determines whether the average count from the storage register is less than the lower limit or greater than the upper limit and, if so, produces a signal indicating that one of the specified limits has been exceeded. Since both registers 120 and 126 are shifted under the control of the same shift signal S, the transfer of the bits $a_i$ is synchronized with the transfer of the bits $b_i$. Accordingly, the first bit (most significant bit) of the average count from the register 120 is supplied to the comparator at the same time as the first bit (most significant bit) of the lower limit data word from the register 126. Similarly, the average count is compared bit by bit with the upper limit data word. The comparator 124 includes a test low input terminal and a test high input terminal which, respectively, receive test enable signals TL and TH from the timing and control section 102. The comparator also includes an output terminal which produces an alarm signal AL which will be discussed later. During the TL signal, which is a binary 1 during the seventh count of the program counter (described below), the comparator is operative to produce an output signal AL of a binary 1 at its output terminal only if a bit in the average count signal $a_i$ is less than the corresponding bit in the lower limit data word, i.e., if the former is a binary 0 when the latter is a binary 1. Since the bits are compared in descending order of significance, the first occurrence of a bit in the signal $a_i$ being less than the corresponding bit in the signal $b_i$ is determinative that the average count is less than the lower limit. The test high signal TH is a binary 1 during the fifteenth count of the program counter and causes the comparator to produce an output signal AL of a binary 1 only if a bit in the average count is greater than a corresponding bit in the upper limit data word. The comparator includes latches L1 and L2 which are selectively set according to the bit comparison and are reset by a reset stage 129 which is connected with the comparator. The latches L1 and L2 are cross-coupled so that only one can be set at a time. The logical relation of the comparator latches and reset stage will be described below in conjunction with the timing and control section. The output of the comparator 124 is supplied to a medical alarm section 106 which will be described subsequently.

The computation section 104, as just described, performs its functions under the control of the timing and control section shown in FIG. 13. The timing and control section comprises the high frequency clock 114 which produces a high frequency clock signal CLH which, in the illustrative embodiment, is at a frequency of 20 kHz. This high frequency clock signal is supplied to the input of the low frequency clock 116 which produces a low frequency clock signal CLL which is nominally 80 Hz in the illustrative embodiment. The output of the low frequency clock is applied to the input of the up/down clock 113.

The high frequency clock signal CLH is represented in the processor timing diagram of FIG. 15. The remaining stages of the timing and control section 102, as illustrated in FIG. 13, will be described with reference to the processor timing diagram. It is noted that this timing diagram represents the high frequency timing cycles of the computation period and, of course, is plotted to a suitable scale for showing pulse rates comparable to the high frequency clock. It is noted from the time scale of FIG. 15, that the computation cycle represented by the timing diagram takes less than 2 milliseconds; the maximum time for a computation cycle in the illustrative embodiment is less than 6 milliseconds. The frequency of the high frequency clock signal CLH determines the speed of operation in the computation cycle. While a frequency of 20 kHz is used in the illustrative embodiment, there are applications, especially in the industrial field, where the frequency may be as high as 5 mHz. In the timing diagram the signals are identified by assigned symbols at the left end of the abscissa; the signal definitions will be given as the signals are encountered in the description that follows.

The timing and control section 102 includes a start stage 130 which is adapted to initiate the computation cycle in response to a logic signal DS from the logic pulse generator 66 of FIG. 4. The start stage 130 has a signal input terminal which receives the logic signal DS and also includes a reset terminal which receives a timing signal Q0 from a program counter 132. The start stage produces a start signal Qs at its output terminal which is applied to the program clock generator 132.

It is noted, with reference to FIG. 15, that the start signal Qs is a pulse which goes high with the logic pulse 68 and remains high until the start stage is reset by the timing pulse Q1. The start signal Qs will then remain low throughout the remainder of the computation period.

A secondary start stage 137 is provided to initiate or restart the program clock 132 under certain conditions in which the start signal Qs is not present. As will be seen subsequently, a program clock output signal CLP is required to cause generation of certain other timing and control signals after the initial program cycle is ended. This will arise after an alarm signal AL has occurred. Additionally, the program clock must be initiated in the absence of a logic pulse DS in case the up/down counter 112 produces an overflow signal OF (to be described later); also, during the programming of the monitor station when a feed signal F is applied the program clock is to be initiated even though there is no logic pulse DS. Accordingly, the secondary start stage 137 has input terminals which receive, respectively, a medical alarm store signal ALA from the medical alarm section 106, a functional alarm store signal ALC from section 108, an overflow signal OF from up/down counter 112 and a feed signal F which is externally supplied. The secondary start stage 137 produces a secondary start signal ST at its output terminal by combining the input signals in accordance with the following logic equation:

$$ST = ALA + ALC + F + OF \qquad (3)$$

In order to provide the timing for the program cycle of the processor, the program clock 132 and the program counter 134 are provided. In the illustrative embodiment, the program for the processor comprises 16 steps and the program clock 132 is adapted to generate a 16 bit clock cycle, represented by the program clock signal CLP, in response to each start signal Qs from the start program state 130 or in response to a secondary start signal ST from stage 137. The 16 bit program cycle will have each program clock pulse synchronized with successive high frequency clock pulses. For this purpose, the program clock 132 has an input terminal which receives the start signal Qs, an input terminal which receives secondary start signal ST, and another input terminal which receives the high frequency clock signal CLH. The program clock 132 also has input terminals which receive timing signals Q0, Q1, Q2 and Q3 from the program counter 134. The program clock 132 produces the program clock signal CLP by combining the input signals according to the following logic equation:

$$CLP = (CLH) \cdot (Qs + Q0 + Q1 + Q2 + Q3 + ST) \qquad (4)$$

With reference to the timing diagram of FIG. 15, it is noted that the program clock signal CLP comprises 16 pulses in synchronism with the high frequency clock pulses, with the first pulse going high at the same time as the first high frequency clock pulse goes high following the time that the start signal Qs goes high. This causes the first stage of the program counter 134 to produce the first pulse of the timing signal Q0 which goes high when the program clock pulse goes low and which goes low when the second program clock pulse goes low. The second stage of the program counter 134 produces the timing signal Q1 in response to Q0; the first pulse of Q1 goes high when the first pulse of Q0 goes low and Q1 goes low when the second pulse of Q0 goes low. Timing signals Q2 and Q3 are produced by the third and fourth stages of the program counter in a similar fashion.

The timing and control section 102 includes a parallel transfer stage 136 which is adapted to produce a parallel transfer signal PT for the down counter 118 and the shift register 120. As mentioned previously, this parallel transfer signal enables the average count computed by the up/down counter 112 to be fed in parallel fashion into the down counter 118 and the register 120. The parallel transfer stage has input terminals which respectively receive the signals Qs and ST. The parallel transfer stage comprises logic elements which produce the parallel transfer signal PT by combining the input signals according to the logic equation:

$$PT = Qs \cdot \overline{ST} \qquad (5)$$

As shown in the timing diagram of FIG. 15, the parallel transfer signal PT comprises a pulse which goes high when the start signal Qs goes high and goes low when the signal Qs goes low, provided the start signal ST is low. Accordingly, the transfer of the average count from the up/down counter 112 is accomplished before the first clock cycle of the program clock signal CLP.

The timing signals produced by the program counter 134 are utilized in the timing and control section 102 to produce additional control signals for the processor. A shift stage 135 has input terminals which receive the high frequency clock signal CLH and the timing signals Q1, Q2 and Q3. The shift state 135 produces a shift signal S which is applied to the shift register 120 and the shift register 126 in the computation section to circulate the bits held in the registers through one complete cycle. The shift stage 135 comprises logic elements which produces the shift signal S by combining the inputs according to the following logic equation:

$$S = (CLH) \cdot (Q1+Q2+Q3) \qquad (6)$$

With reference to the timing diagram of FIG. 15, it is noted that the shift signal S comprises a series of fourteen pulses in synchronism with the program clock signal CLP.

For the purpose of resetting the up/down counter 112 in the computation section after the counter is incremented by the low frequency clock pulses, a down-clock stage 138 is provided in the timing and control section 102. The down-clock stage produces a down-clock signal CLD which is applied to the down-count input terminal of the down-counter 118. To produce the down-clock signal, the down-clock stage includes input terminals which receive the high frequency clock signal CLH, the parallel transfer signal PT and the count zero zignal CZ, respectively. The down-clock signal CLD is produced by logic circuits which combine the input signals according to the logic equation:

$$CLD = CLH \cdot \overline{CZ} \cdot PT \qquad (7)$$

The down-clock signal CLD, as shown in FIG. 15, is a pulse train at the frequency of the high frequency clock signal CLH and synchronized therewith. It is initiated when the parallel transfer signal PT goes low and it continues until the down-counter 118 is counted down to zero as signified by the count zero signal CZ going high. As previously mentioned, when the zero count is reached in the down-counter 118 the count zero signal CZ is produced by the down-counter and applied to the up/down clock 113 to condition it for counting up. Thus the up/down counter is placed in readiness for receiving an incrementing count from the low frequency clock as soon as the computation period is ended. The count zero signal CZ, as shown in FIG. 15, goes low at the time the parallel transfer signal PT goes high and it remains low until the last pulse of the down-clock signal CLD goes high. It is noted that the number of pulses in the down-clock signal is equal to the previous average count from the up/down counter and this number, in the illustrative embodiment, exceeds the number of pulses in the program clock signal CLP. Consequently, the signal of greatest duration during the computation period is the down-clock signal which, as previously noted, is less than 2 milliseconds and is well within the time duration of the heartbeat signal from which the logic pulse 68 is developed.

The timing and control section 102 also includes a test-low stage 140 and a test-high stage 142 which respectively produce test-low signal TL and test-high signal TH for control of the comparator 124. The test-low signal TL is used in the comparator 124 in a manner, described below, so that the comparator produces an alarm signal AL only if the average count is lower than the low-limit count. The bit-by-bit comparison is made during the circulation of the signals ai and bi through a shift cycle produced by the first seven pulses of the shift signal S. The test-low stage 142 has input terminals which receive the timing signals Q0, Q1, Q2 and Q3. The stage 140 comprises logic elements which produce the test-low signal TL by combining the input signals in accordance with the following logic equation:

$$TL = \overline{Q3} \cdot (Q0 \cdot Q1 \cdot Q2) \qquad (8)$$

As indicated on the timing diagram of FIG. 15, the test-low signal TL goes high during the seventh count of the program counter.

The test-high signal TH is used in the comparator 124 in a manner, described below, to produce an alarm signal AL only if the average count is higher than the high-limit count. The test-high stage 142 has input terminals which receive the timing signals Q0, Q1, Q2 and Q3. This stage produces the test-high signal TH by combining the input signals according to the following logic equation:

$$TH = Q3 \cdot (Q0 \cdot Q1 \cdot Q2) \qquad (9)$$

As shown in FIG. 15, the test-high signal TH goes high during the fifteenth count of the program counter.

The comparator 124 was described above in connection with the computation section 104. It will be recalled that the comparator is adapted to produce an alarm signal AL in the event that the average count supplied from the storage register 120 falls outside of the lower and upper limits supplied from the shift register 126. The alarm signal AL goes high, i.e., is a binary 1, upon the determination that the average count is below the lower limit or above the upper limit. The determination is made in the following manner: latch L1 is set to a binary 1 by the condition $(\bar{a}_i b_i)$, and latch L2 is set by the condition $(a_i \bar{b}_i)$, while both latches are reset to the zero state by signal RAL, where:

$$RAL = \overline{(Q0+Q1+Q2)} \qquad (10)$$

The reset signal RAL is generated by the reset stage 129 within the comparator circuit block. The latches L1 and L2 are cross-coupled in such a manner, that once one is set to binary 1 state, the other is held in the zero state until both are reset by signal RAL. At the beginning of the computation cycle the reset signal RAL is binary 1, thus both latches are held in the zero state; during the comparison of the low limit and the current average value the latches are free to change state, and the first unequal bit pair will set latch L1 to the binary 1 state; no further change is possible until the end of the comparison. During the time interval when the least significant bits $(a_1, l_1)$ are compared, the test low signal TL is a binary 1, and an alarm signal AL is generated if the output of latch L1, signal QL1, is a binary 1. The reset signal becomes a binary 1 during the eighth count of the program counter, thus resetting both latches to the zero output condition. During the next seven clock cycles the current average value is compared to the high limit. The first unequal bit pair sets the latch L2 to the binary 1 state, while locking the latch L1 to the zero state. The test high signal TH is a binary 1 during comparison of the least significant bits $(a_1, h_1)$, and an alarm signal AL is sent if the output of latch L2, signal QL2, is a binary 1, indicating that the average value is larger than the high limit. The alarm conditions are expressed by the following logic equation:

$$AL = TL \cdot QL1 + TH \cdot QL2 \qquad (11)$$

The alarm signal AL sets the medical alarm store 146 so that the signal ALA is a binary 1. The alarm store will be reset by signal Qe to the binary zero state after the completion of the alarm transmission.

As discussed above, the processor includes a medical alarm section 106 which will now be described with reference to FIG. 14. The medical alarm section 106 is adapted to initiate the transmission of an emergency signal via the radio link to the central station. As discussed above, this emergency signal, in the case of a medical alarm, comprises an indefinite number of bursts of the identification code word. The medical alarm store 146 has an input terminal which receives the medical alarm signal AL from the comparator 124. It also has a reset terminal which receives a reset signal Qe from the alarm transmitter and control section 110. The medical alarm store 146 functions in the manner of a bistable flip-flop and is set by the alarm signal AL and is reset by the reset signal Qe. When the alarm store is set it produces the alarm store signal ALA. This alarm store signal ALA is a pulse, as shown in FIG. 11, which remains high until reset by Qe. The medical alarm store signal ALA is applied to one input of the secondary start stage 137, as mentioned above.

In the alarm and transmitter control section 110, a shift code stage 148 is adapted to produce a shift code signal SC which is used for controlling transmission of the emergency signal. The shift code stage includes an input terminal which receives a signal Qa from an alarm counter 154 and another input terminal which receives the shift signal S. The signal Qa is held low when there is no alarm and is counting if there is an alarm store signal ALA (or ALC). This stage produces the shift code signal SC by combining the input signals according to the following logic equation:

$$SC = S \cdot Qa \qquad (12)$$

The shift code signal SC comprises a pulse train which is in synchronism with the shift signal S when present but which is absent unless there is an ST signal. This shift code signal is applied to one input of the shift register 122.

The functional alarm section 108 is similar to the medical alarm section 106, except that it is adapted to initiate transmission of an emergency signal in case of a malfunction in the monitor station. The functional alarm section comprises an out-of-contact sensor 152 which is adapted to produce a contact signal $\bar{C}$ in the event that the monitor station (wrist-unit 30) becomes physically separated from the patient to which it is assigned. This sensor 152 suitably comprises a pressure responsive switch which is in a closed condition when the wrist-unit is making suitable contact with the body of the patient.

The functional alarm section also includes a low battery sensor 153 which is adapted to detect the occurrence of an unduly low voltage produced by the battery 44 in the wrist-unit. This sensor suitably comprises a voltage detector having a predetermined threshold and which produces a low voltage signal BL when the voltage of the battery falls below the predetermined level.

The functional alarm section 108 includes a functional alarm generator 156. This generator 156 has input terminals which receive the contact signal $\bar{C}$ and the low voltage signal BL. The generator includes an output terminal and produces a functional alarm signal AL' upon receipt of either input signal V or $\bar{C}$. The functional alarm signal AL' is applied to a functional alarm store 158.

The functional alarm store 158 is adapted to produce a functional alarm store signal ALC in response to receipt of the functional alarm signal AL'. The alarm store 158 is suitably of the same circuitry as the medical alarm store 146 described above. Accordingly, it has a reset terminal which receives a reset signal Qd from the alarm counter 154 in the transmitter and control section 110, to be described subsequently. The functional alarm store 158 is set upon receipt of the functional alarm signal AL' at its input terminal and thereupon produces the alarm store signal ALC. This signal comprises a pulse which is identical to the alarm store signal ALA shown in FIG. 11. The functional alarm store signal ALC is applied to the secondary start stage 137, as discussed above.

The shift code stage 148 produces a shift code signal SC in response to the functional alarm store signal ALC to control transmission of the emergency signal in the same manner as in the case of a medical alarm. This occurs because the signal Qa is produced by the alarm counter 154 in response to a functional alarm store signal in the same way as a medical alarm store signal.

The shift code signal SC from the shift code stage 148 is applied to the shift code input terminal of the shift register 122, as previously mentioned. The shift register 122 is adapted to respond to the shift code signal by circulating the identification code word, ID + Y, to the output in a bit-by-bit fashion to produce a serialized identification signal IDS. This signal is made up of the bits of the identification code word and the bits occur in synchronism with the shift code signal. The serialized identification signal IDS is a serial form of the identification code word ID + Y shown in FIG. 11 and is applied in serial fashion, by the shift register 122, to one input of the transmit code stage 150.

The transmit code stage 150, along with the previously mentioned shift code stage 148 is a part of the transmitter and control section 100. In addition, this section includes the alarm counter 154. The alarm counter 154 is adapted to count and control the number of times the serialized identification signal IDS is transmitted. It will be recalled that in the case of a medical alarm it is desired to transmit a burst of sixteen IDS signals followed by a delay of about four seconds and then repeat the burst and delay, over and over. In case of a functional alarm, it is desired to transmit a burst of four IDS signals and then terminate the transmission. In order to count and control the number of times the IDS signal is transmitted, the alarm counter 154 is adapted to count the repetitions of the IDS signal and to reset the alarm store when a predetermined count is reached. When an emergency signal transmission is initiated each IDS signal, i.e., each serialized form of the identification code word ID + Y requires a complete program cycle for transmission. Since a single Q3 signal occurs during each program cycle it is convenient to have the alarm counter 154 count the number of Q3 signals as a measure of IDS signals. Accordingly the alarm counter 154 has an input terminal which receives the signal Q3. This counter is a five stage ripple counter having output terminals which respectively produce output signals Qa, Qd and Qe. The output signal Qa is taken from the output of the first stage. As previously mentioned, the output signal Qa is applied to one input of the shift code stage 148 and with the shift signal S causes production of the shift code signal SC. The output signal Qd is taken from the fourth stage of the alarm counter and is applied, as previously mentioned, as a reset signal to the functional alarm stage 158. The output signal Qe from the alarm counter is taken from the fifth stage thereof and is applied as a reset signal to the reset input of the medical alarm store 146. The alarm counter 154 has a reset input terminal which receives the signal ST from the secondary start stage 137. The alarm counter is reset when the signal ST goes to a logical low or zero; hence, the alarm counter is incremented upon the occurrence of each Q3 pulse when the signal ST is at a logical high or 1 which obtains whenever there is an alarm store signal ALA or ALC or OF or F.

The output of the transmit code stage 150 is applied to the amplifier stage of the transmitter to transmit the emergency signal T via the radio link to the central station. The transmit code stage has input terminals which receive, respectively, the serialized identification signal IDS from the shift register 122, the program clock signal CLP from the program clock and the signal Qa from the alarm counter. The transmitter produces the emergency signal T by combining the input signals according to the following logic equation:

$$T = IDS \cdot CLP \cdot Qa \qquad (13)$$

When the transmitter stage receives the signal $IDS$, the signal $Qa$ and the signal $CLP$ the emergency signal $T$ is transmitted. This signal, as shown in FIG. 11, is the identification code word ID + Y with fourteen bits occurring in synchronism with the shift code signal SC.

OPERATION OF THE MONITOR SYSTEM

The monitor system, as just described with reference to the illustrative embodiment, is especially adapted for use in a hospital to monitor the heartbeat rate of a plurality of patients. For this purpose, each patient is assigned a monitor station 10 in the form of a wrist-unit 30. The wrist-unit assigned to a given patient is programmed at the central station 12 to adapt it to the patient's requirements. This includes loading of the memory with the data words B and identification code word ID + Y, as previously described with reference to FIG. 8. This data word B specifies the acceptable range of variations of heartbeat rate for the patient in terms of the lower limits and the upper limits, as defined by the patient's physician. The upper and lower limits of heartbeat rate are defined by the physician as a number of heartbeats per minute and the numbers for the lower and upper limits are stored in the memory of the wrist-units in binary form with 7 bit positions allotted to each number. The identification code word comprises the identifier code ID which is the name of the patient to whom the wrist-unit is assigned. This code word also includes the programming code Y which specifies the number of heartbeats to be used for determining the average heartbeat rate. The identification code word is stored in the memory of the wrist-unit in binary form with fourteen bit positions allotted to this word; 11 bit positions are allotted to the identifier code ID and three bit positions are allotted to the programming code Y. It is to be noted that the number of bit positions in the memory of the wrist-unit for the data word B and for the identification code word ID + Y is much greater than that required for the numbers applicable to monitoring a patient's heartbeat; this amount of memory capacity, however, is allotted because the same wrist-unit may be used for monitoring other life functions which require greater data storage capacity.

Figure 9:
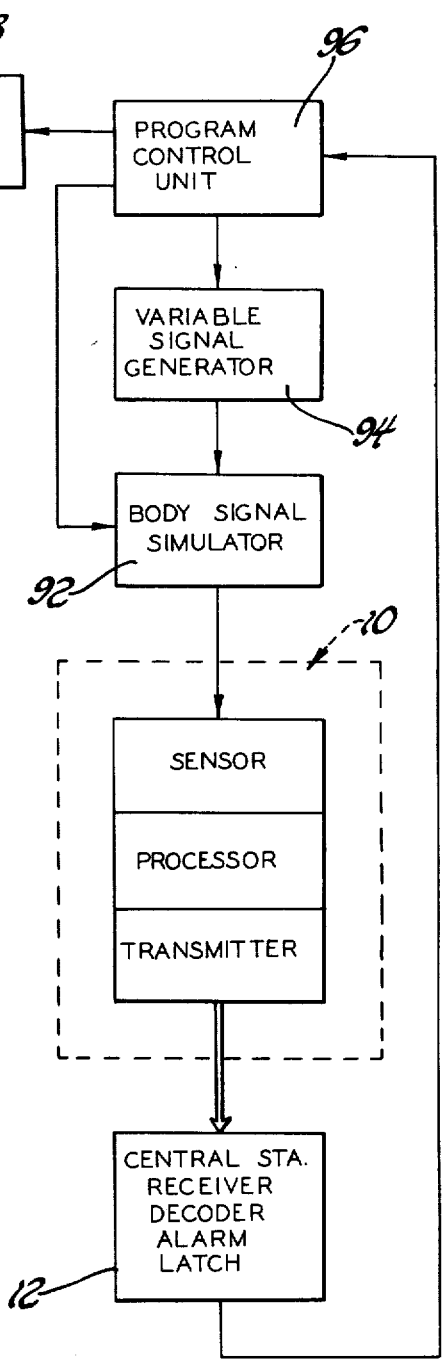
FIG. 9 is a block diagram of a test apparatus for the monitor station.

After the wrist unit is programmed, it is subjected to a test at the central unit 12 as previously described with reference to FIG. 9. After the monitor station is tested it is attached to the patient in a manner of a wristwatch and thereby placed in operation.

The operation of the digital processor of the monitor station will be described with reference to FIGS. 12, 13 and 14 and the timing diagrams of FIGS. 10, 11 and 15. The sensor of the monitor station produces an electrical signal in response to each heartbeat of the patient and the signal processing stages of the monitor station (FIG. 4) develop a logic pulse 68 corresponding to each heartbeat. As shown in FIG. 10 the succession or train of logic pulses 68 constitute the logic signal DS which is applied to the digital processor at the input of the start program stage 130. Each logic pulse 68 is about 1 millisecond duration and upon the occurrence of the pulse the computation period is initiated. The computation is performed after each heartbeat pulse and will require up to about 2 milliseconds. The logic pulses 68 have a pulse period which varies with the heartbeat rate from about ½ second up to about 2 seconds.

The heartbeat rate is measured by means of the low frequency clock 116 which produces the clock signal CLL. This low frequency clock signal is applied to an input of the up/down clock 113 which produces the output signal CLA which is applied to the count input of the up/down counter 112. When the down counter 118 is empty and produces a counter zero signal CZ which is a logical high the signal CLA is a pulse train identical to the low frequency clock signal CLL. Thus the up/down counter 112 commences to count up upon the occurrence of the logic pulse 68. (The up/down counter 112 was previously incremented during the programming operation so that it holds a count equal to a normal heartbeat rate.) The counter 112 is provided with the data word input W to establish the averaging period for determining the heartbeat rate. The data word W specifies the divisor for the counter 112 and is provided by the decoder 121 which receives the programming word Y from the shift register 122. The programming word Y is a binary number indicative of the number of heartbeats which is to be used for computing the average heartbeat rate. The number of heartbeats over which the average is taken in the illustrative example is eight and accordingly the total accumulated count in the counter 112 is to be divided by eight. This division is performed in binary by shifting the registered count by three bit positions from the most significant bit toward the least significant bit. The output of the counter 112 thus represents the average heartbeat rate over the last eight heartbeats. This average, in the illustrative embodiment, is an approximation in that the accumulated count is the total of the last nine heartbeats minus the approximated average of the last eight heartbeats (i.e., instead of subtracting a count equal to the rate of the ninth preceding heartbeat the average of the last eight is subtracted). Before describing further operation of the computation section shown in FIG. 12, reference is made to the operation of the timing and control section of FIG. 13.

When the logic signal DS is applied to the start program stage 130 a start signal Qs is produced thereby and is applied to the program clock 132 and to the parallel transfer stage 136. The program clock 132, which receives the high frequency clock signal CLH, is thus initiated and produces the program clock signal CLP which comprises a program cycle of sixteen high frequency clock pulses. The output of the program clock is applied to the input of the prograam counter 134 which is a four stage ripple counter and which produces the output signals Q0, Q1, Q2 and Q3 from the successive stages. These timing signals are fed back to the program clock and to certain other of the timing and control stages. The output Q0 is applied to the input of the program start stage 130 to reset the start signal Qs. The start signal Qs, as the sole input to the parallel transfer stage 136, is effective to produce a parallel transfer signal PT. This parallel transfer signal is applied to both the down counter 118 and the shift register 120 in the computation section. This causes the average count represented by bit positions A6 through A12 in the up/down counter 112 to be transferred in parallel fashion to the down counter 118 and the shift register 120. This average count is the approximated average based upon the preceding eight heartbeats. The parallel transfer signal PT is also applied to one input of the down clock 138 in the timing and control section. This down clock also receives the high frequency clock signals CLH from the high frequency clock 114 and the counter zero signal CZ from the down counter 118. As shown in the timing diagram of FIG. 15 the down clock 138 is operative to produce the down count signal CLD when the parallel transfer pulse goes low and when the count zero pulse is low. This down count signal CLD is a pulse train in synchronism with the high frequency clock signal and is applied to the up/down clock 113 and the down counter 118 in the computation section. When the down count signal CLD is applied to the up/down clock and with the count zero signal at a logical low, the clock 113 produces an output signal CLA having a pulse rate equal to that of the high frequency clock signal CLH. This output signal CLA of the up/down clock 113 is applied to the count input of the up/down counter 112 and at the same time the down count signal CLD is applied to the input of the down counter 118. Accordingly, the down counter and the up/down counter are decremented at the rate of the high frequency clock signal until the down counter reaches zero at which time it causes the output count zero signal CZ to go to logical high. This signal CZ is applied to one input of the down clock 138 and terminates the down count signal CLD. The signal CZ, when it is at logical high, causes the up/down clock 113 to produce an output signal CLA in synchronism with the low frequency clock signal CLL. Thus the up/down counter 112 is operated to compute the average heartbeat rate for the preceding eight heartbeat cycles and the number representing this average has been transferred to the shift register 120 in the bit positions a1 through a7. Also the up/down counter 112 and the down counter 118 have been counted down or decremented by this newly computed average number so that the down counter is empty and the up/down counter is reset for counting up during the current heartbeat period at the rate of the low frequency clock.

During this same computation period the comparator 124 is operative to determine whether the new average count which represents the heartbeat rate is within the upper and lower limits as specified by the physician during the programming of the monitor station. The comparator 124 receives at one input the signal ai from the shift register 120 and receives at another input terminal the signal bi from the shift register 126. The signal ai is a serialized form of the binary number stored in the shift register 120 which represents the computed average count for the heartbeat rate. The signal bi is a serialized form of the data word B which was applied during programming to establish the lower and upper limits of the count for the heartbeat rate of the patient. The first 7 bits of the data word B represent the lower limit and the last seven bits represent the upper limit. (It will be recalled that although the physician specifies the limits in terms of heartbeats per minute the data converter 84, during programming, translates this specification into a number of low frequency clock pulses. Also during the programming the number of low frequency clock pulses is adjusted to correct for any deviation of the low frequency clock rate from its normal or standard rate.) To effect the comparison of the average count in the shift register 120 with the lower limit count in the shift register 126, the timing and control section produces a test low signal TL from the test-low stage 140 during the seventh program count of the program cycle and produces a test high signal TH from the test-high stage 142 during the fifteenth program count. These signals, TL and TH, are applied to the comparator 124 in the timed relation as indicated in the timing diagram of FIG. 15. The shift stage 135 of the timing and control section produces a shift signal S which is simultaneously applied to the input of the shift register 120 and the input of the shift register 126. As noted in the timing diagram of FIG. 15 the shift signal comprises 14 successive pulses synchronized with the high frequency clock signal CLH and is operative to circulate the bits representing the average count through the seven bit positions in the shift register 120 and synchronously circulate the bits of the data word B representing the lower and upper limits through the 14 bit positions of the shift register 126. This produces the serialized signals $ai$ and $bi$ and presents them to the comparator 124 for comparison on a bit-by-bit basis. As discussed previously, the comparison of bits starts with the most significant bit and advances through the successively less significant bits. If the comparator determines that the average count is out of limits the alarm signal goes to logical high. The alarm signal AL is applied to the input of thhe medical alarm store 146 shown in FIG. 14.

Assuming the average count in the shift register 120 represents a heartbeat rate which is within the specified limits, the computation cycle just described above will be completed as shown in the timing diagram of FIG. 15. If, however, the average count held in the shift register 120, after a subsequent heartbeat, is less than the specified lower limit or greater than the specified upper limit of the heartbeat rate the comparator output signal AL will go to logical high. This condition is illustrated in the timing diagram of FIG. 10 which shows that the computation period 3 which follows the pulse period 2 determines that the count C2 of the pulse period 2 was sufficiently low to indicate the average heartbeat rate exceeds the upper permissible limit of heartbeat rate. Consequently the comparator 124 produces the output pulse 69, i.e., the signal AL goes to logical high. As shown in FIG. 11, this causes the alarm store signal ALA to go to logical high. As further shown in the timing diagram of FIG. 10, the occurrence of the alarm store signal ALA causes the monitor station to transmit the emergency signal T which will be discussed further below. The time duration of the emergency signal T is relatively small on the time scale of the timing diagram of FIG. 10 and hence it will be described further with reference to the timing diagram of FIG. 11 which is plotted to a larger time scale.

The alarm signal AL, as previously mentioned, is applied to the medical alarm store 146 and when the signal AL goes to logical high the alarm store 146 causes the alarm store signal ALA to go to a logical high. This alarm store signal ALA is applied to one of the inputs of the secondary start stage 137 in the timing and control section. When any of the inputs of this secondary start stage is at logical high the output signal ST is also at logical high. This start signal ST is applied to a start input of the program clock 132 and is effective to restart the program clock for a subsequent cycle when the alarm signal AL goes high during the preceding program cycle. This start signal ST is also applied to one input of the parallel transfer stage 136 and when the signal ST is logical high it inhibits the production of the parallel transfer pulse PT. At the beginning of the next program cycle the program clock signal CLP is initiated to time the successive program cycles as indicated by the pulse train 160 of FIG. 11. Accordingly, the Q3 signal, also shown in FIG. 11, is produced and as indicated in FIG. 14, is applied to the input of the alarm counter 154. This Q3 pulse 162 increments the alarm counter so that the first stage thereof causes the signal Qa to go to logical high. This signal is applied to one input of the shift code stage 148 which receives at its other input the shift signal S from the shift stage 135. Accordingly, the shift code stage 148 produces the output shift code signal SC. The shift code signal SC is applied to the input of the shift register 122 in the computation section shown in FIG. 12. This shift code signal causes the bits of the identification code word ID + Y to be circulated around the fourteen bit positions in the register. Accordingly, the shift register 122 produces the output signal IDS which is applied to one input of the transmit code stage 150 in the transmitter and control section 110 shown in FIG. 14. The stage 150 also has inputs which receive the program clock signal CLP and the output signal Qa from the alarm counter 154. When these signals are all high simultaneously the transmitter output signal T goes high and produces the pulse train shown in FIG. 11. It is noted that this comprises a burst of sixteen identification code words followed by a delay interval of approximately 4 seconds. This pattern of the bursts and delay, is repeated an indefinite number of times. This pattern is transmission signal T and is controlled as follows. During the first program cycle after the alarm signal AL occurs the medical alarm store signal ALA causes the secondary start stage 137 to hold the start signal ST at logical high and therefore keeps the program clock 132 running. This causes the shift signal S to be repeated and therefore the serialized identification signal IDS is produced by the shift register 122. For each output of serialized identification signal, i.e., each identification code word in serialized form, signal Q3 is produced and applied to the alarm counter 154. Accordingly, the alarm counter is incremented once for each serialized identification signal and after sixteen serialized identification signals the fifth stage of the alarm counter 154 causes the signal Qe to go high. This signal is applied as a reset signal to the medical alarm store 146 which causes the alarm store signal ALA to go low. As a result the start signal ST of the secondary start stage 137 goes low and the program clock 132 stops running. This also stops the shift signal S and the emergency signal transmission is stopped. The clocks 114 and 116 continue to run and after a period of about four seconds the up/down counter 112 overflows and produces the overflow signal OF at a logical high. This overflow signal OF is applied to the secondary start stage 137 and the start signal ST goes to logical high and restarts the program clock which in turn causes the shift signal S to be produced by the shift stage 135. The up/down counter 112 is emptied at overflow and is ready to start counting. It is still set for counting up and receives the low frequency clock signal CLL. The comparator 124 applies the medical alarm signal AL to the medical alarm store which causes the signal ALA to go high. The signal ALA now causes the secondary start stage 137 to hold the start signal ST at logical high and to keep the program clock running. Thus the whole cycle of producing the burst of sixteen identification code signals and the four second delay period is repeated. The same entire cycle will be repeated over and over until the alarm is answered and the monitor station is manually deactivated or until the battery of the monitor station is exhausted.

The operation in the event of a functional alarm is in many respects similar to that just described for a medical alarm. In case the wrist-unit is removed from the patient the out-of-contact sensor 152 will produce a signal $\overline{C}$ which is applied to the functional alarm generator 156. If the battery of the monitor station becomes run down, the low battery sensor 153 will produce a signal BL which is applied to the input of the functional alarm generator 156. Either signal $\overline{C}$ or BL will cause the alarm generator to produce a functional alarm signal AL' which is applied to the input of the functional alarm store 158. This causes the alarm store to produce an output signal ALC which is applied to one input of the secondary start stage 137. This stage produces the start signal ST which is applied to the program clock 132 and restarts the program clock for the subsequent program cycle. The alarm counter 154 is incremented by the signal Q3 causing the first stage of the counter to produce the signal Qa at a logical high. This signal Qa is applied to the shift code stage 148 to produce the shift code signal SC. The signal SC is applied to the shift register 122 and the serialized identification signal is produced thereby. This is applied to the transmitter stage 150 and the emergency signal T is initiated. After transmission of four identification code words ID + Y, the fourth stage of the alarm counter 154 causes the signal Qd to go high. This signal is applied to the reset input of the functional alarm store 158 and the alarm store signal ALC goes low. This causes the start signal ST from the secondary start stage 137 to go low and the program clock 132 is stopped. This terminates the transmission of the emergency signal T. If the functional alarm is caused by the off-arm sensor 152, the program clock 132 cannot be restarted since the sensor is unable to produce the heartbeat signal and hence there will be no logical pulse DS input to the start program stage 130. The functional alarm signal ALC will remain low after being reset by the signal Qc because a complete up/down cycle of C is needed to set the functional alarm store signal ALC to binary 1. Thus in the case of the removal of the monitor station from the patient, the transmitter will emit a burst of eight identification code words and then transmission will stop for good. If the functional alarm is caused by the low battery sensor 153, the sequence of actions is identical to that described for the off-arm functional alarm.

It is to be noted that a monitor system is adapted for multiple monitor stations for each central station. All of the monitor stations transmit on the same radio frequency and all monitor stations transmit emergency signals as described above. Because of the timing pattern of the transmission of the emergency signals the likelihood of interference of emergency signals from two more monitor stations is minimized. Even though two monitor stations have a medical alarm or functional alarm occurring at about the same time the transmission of the burst of identification code words from one monitor station will probably not coincide with the burst from the other monitor station because the burst period is so small compared to the delay period between bursts. At the frequencies in the illustrative embodiment, the medical alarm burst requires 24.8 milliseconds and the functional alarm burst requires 11.2 milliseconds, whereas the delay between medical alarm bursts is about four seconds duration. Accordingly, the transmission bursts from different monitor stations will be interleaved in the time pattern without any interference with each other. Unless the transmission bursts of code words from two monitor stations occur precisely at the same time, the worst case would be the time coincidence of some of the code words in a given burst. But then, due to the number of code words in each burst, at least the first code word in the burst from one station and the last code word in the burst from the other station would be free of interference. This scheme of emergency transmission makes possible the use of a common radio frequency for all monitor stations.

Although the description of this invention has been given with reference to a particular embodiment, it is not to be construed in a limiting sense. Many variations and modifications of the invention will now occur to those skilled in the art. For a definition of the invention reference is made to the appended claims.

The embodiments of the present invention in which an exclusive property or privilege is claimed are defined as follows:

1. A patient monitoring system for plural persons, said system comprising plural individual monitor units each being adapted to be associated with a different person and movable therewith, each unit including a sensing means adapted to be operatively connected with the associated person and responsive to a body condition to produce a body condition signal, signal processing means connected with the sensing means and including limit detecting means for producing a recurrent alarm signal each time the body condition signal deviates beyond a predetermined limit, first memory means storing the value of said limit and connected with said limit detecting means, each unit also including a signal transmitting means adapted to transmit an emergency message comprising at least one occurrence of an identifier code corresponding to said monitor unit, each said emergency message having a duration which is several times shorter than the interval between alarm signals, second memory means for storing said identifier code, control means connected between said second memory means and said signal transmitting means for applying said emergency message to the transmitting means each time said alarm signal occurs, said control means being exclusively responsive to said alarm signal for initiating transmission of said emergency message, said control means of each monitor unit being independent of the other monitor units of the system with the respective alarm signals occurring independently so that the respective emergency messages of two monitor units may be initiated at any time relative to each other but with at least one identifier code of at least one emergency message of each monitor unit occurring in the time interval between the emergency messages of the other unit, said system also comprising a central station including a signal receiving means, said control means causing the signal transmitting means to initiate transmission as aforesaid independently of any control by the central station, decoding means connected with the receiving means for producing a decoded identifier code in response to receipt of an emergency message, and annunciating means connected with said decoding means and responsive to a decoded identifier code for presenting the identifier code of the monitor unit which produced an alarm signal.

2. The invention as defined in claim 1 wherein said sensing means produces an analog condition signal, and said signal processing means is a digital data processor with a computation section which includes said limit detecting means, and an analog to logic level converting means connected between said sensing means and said computation section, said converting means being responsive to an attribute of the analog signal to produce a train of logic pulses having a frequency corresponding to the value of the body condition.

3. The invention as defined in claim 2 wherein said limit detecting means comprises memory means for storing a data signal corresponding to said predetermined limit for the value of said condition signal, and comparator means having inputs connected with said converter means and said memory means for comparing the value of the condition signal with the predetermined limit.

4. The invention as defined in claim 3 including threshold means connected between said sensing means and said converter means.

5. The invention as defined in claim 4 wherein said signal processing means includes first clock means having a frequency higher than the frequency of the logic pulses, counting means connected with said converting means and said clock means for counting the clock pulses between said logic pulses whereby said count of clock pulses is indicative of the time between said logic pulses and, hence, the value of the body condition.

6. The invention as defined in claim 5 wherein the counting means accumulates the number of clock pulses over a predetermined number of periods of logic pulses, averaging means connected to said counting means and said comparator means for producing an average value of the clock pulses per period said average value being the average value of the body condition for comparison with the predetermined limit.

7. The invention as defined in claim 6 wherein said counting means is an up/down counter, decrementing means connected with the counting means for decreasing the count after each period by an amount approximately equal to the count for the first period of said predetermined number of periods.

8. The invention as defined in claim 7 wherein said memory means includes a first register, and said averaging means comprises means connected with said up/down counter for transferring bits from the counter to the first register with the bit positions shifted to perform binary division by a divisor equal to the number of periods.

9. The invention as defined in claim 8 wherein the decrementing means is connected with said first register whereby the up/down counter is decremented by the average count for the previous predetermined number of periods.

10. The invention as defined in claim 8 including control means connected with said clock means and with said averaging means and said comparator means to cause operation thereof in a computation period immediately following each logic pulse.

11. The invention as defined in claim 10 including second clock means having a frequency higher than said first clock means and being connected with said decrementing means to control the decrementing rate thereof.

12. The invention as defined in claim 11 wherein said memory means includes a second register for storing said data signal, said first and second registers being adapted to store data in binary form, said comparator means being of the one-bit type, said control means including shift means connected with said registers for transferring the counts in said registers bit-by-bit to the respective inputs of the comparator means in descending order of bit significance, said comparator producing said alarm signal in response to a bit comparison indicative of a body condition signal which exceeds said predetermined limit.

13. The invention as defined in claim 12 including a first alarm store connected with the output of the comparator means and responsive to an alarm signal for producing a first alarm store signal, a third register adapted to store the identifier code of the monitor unit, said first alarm store being connected with the third register to cause said identifier code to be applied to said transmitting means, and first alarm counting means for causing said identifier code to be applied to said transmitting means a number of times in excess of a predetermined number.

14. The invention as defined in claim 12 wherein said second register of the memory means includes first and second portions for storing first and second data signals corresponding to lower and upper limits, respectively, for the value of said condition signal.

15. The invention as defined in claim 12 wherein said central station comprises a time generator adapted to produce successive timing pulses separated by an adjustable time interval, a calibrating counter, circuit means for connecting the first clock output of one of said monitor units to said calibrating counter, means for adjusting said time generator according to a desired limit of the value of said body condition, said circuit means being adapted to stop and start said calibrating counter upon the occurrence of successive pulses from said timing generator whereby said second register in said monitor unit may be preset according to a prescribed limiting body condition value for a given patient.

16. The invention as defined in claim 13 including a malfunction detecting means connected with a selected portion of said monitor unit, a second alarm store connected with the malfunction detecting means and with said third register to cause said identifier code to be applied to said transmitting means, and second alarm counting means for causing said identifier code to be applied to said transmitting means a number of times equal to said predetermined number.

17. The invention as defined in claim 1 wherein said sensing means comprises a transducer for producing an electrical signal indicative of the occurrence of successive heartbeats.

18. The invention as defined in claim 17 wherein said transducer comprises at least two electrodes adapted to be electrically connected to the body of the patient.

19. A patient monitor unit comprising a sensing means adapted to be operatively connected with a patient and responsive to a body condition thereof to produce a body condition signal, first memory means for storing a data signal corresponding to a predetermined value of said body condition, comparator means connected with said sensing means and said first memory means for producing a recurrent alarm signal each time the body condition signal deviates beyond the predetermined value, said unit also including a signal transmitting means connected with said comparator means and adapted to transmit an emergency message comprising at least one occurrence of an identifier code corresponding to said monitor unit, each said emergency message having a duration which is several times shorter than the interval between alarm signals, second memory means for storing said identifier code, control means connected between said second memory means and said signal transmitting means for applying said emergency message to the transmitting means each time said alarm signal occurs, said control means being exclusively responsive to said alarm signal for initiating transmission of said emergency message, whereby emergency messages may be transmitted by the monitor unit at any time relative to the emergency message of another monitor unit but with at least one identifier code of at least one emergency message of the monitor unit occurring in the time interval between the emergency messages of said another monitor unit, said control means being independent of any signal originating externally of the monitoring unit.

20. The invention as defined in claim 19 wherein said sensing means produces an analog condition signal, said first memory means and said comparator means being parts of a computation section in a digital data processor, an analog to logic level converting means connecting between said sensing means and said computation section, said converting means being responsive to an attribute of the analog signal to produce a train of logic pulses having a frequency corresponding to the value of the body condition, and threshold means connected between said sensing means and said converting means.

21. The invention as defined in claim 20 wherein said signal processing means includes first clock means having a frequency higher than the frequency of the logic pulses, counting means connected with said converting means and said clock means for counting the clock pulses between said logic pulses.

22. The invention as defined in claim 21 wherein the counting means accumulates the number of clock pulses over a predetermined number of periods of logic pulses, averaging means connected to said counting means and said comparator means for producing an average value of the clock pulses per period, said average value being the average value of the body condition for comparison with predetermined value.

23. The invention as defined in claim 22 wherein said counting means is an up/down counter, decrementing means connected with the counting means for decreasing the count after each period by an amount approximately equal to the count for the first period of said predetermined number of periods.

24. The invention as defined in claim 23 wherein said averaging means includes a first register connected with said up/down counter with means for transferring bits from the counter to the register with the bit positions shifted to perform binary division by a divisor equal to the number of periods.

25. The invention as defined in claim 24 wherein the decrementing means is connected with said register whereby the up/down counter is decremented by the average count for the previous predetermined number of periods.

26. The invention as defined in claim 24 including control means connected with said clock means and with said averaging means and said comparator means to cause operation thereof in a computation period immediately following each logic pulse.

27. The invention as defined in claim 26 including second clock means having a frequency higher than said first clock means and being connected with said decrementing means to control the decrementing rate thereof.

28. The invention as defined in claim 27 wherein said memory means for storing said data signal comprises a second register, said first and second registers being adapted to store data in binary form, said comparator means being of the one-bit type, said control means including shift means connected with said registers for transferring the counts in said registers bit-by-bit to the respective inputs of the comparator means in descending order of bit significance, said comparator producing said alarm signal in response to a bit comparison indicative of a body condition signal which exceeds said predetermined limit.

29. The invention as defined in claim 28 including a first alarm store connected with the output of the comparator means and responsive to an alarm signal for producing a first alarm store signal, said second memory means including a third register adapted to store the identifier code of the monitor unit, said first alarm store being connected with the third register to cause said identifier code to be applied to said transmitting means, and first alarm counting means for causing said identifier code to be applied to said transmitting means a number of times in excess of a predetermined number.

30. The invention as defined in claim 28 wherein said second register of the memory means includes first and second portions for storing first and second data signals corresponding to lower and upper limits, respectively, for the value of said condition signal.

31. The invention as defined in claim 29 including a malfunction detecting means connected with a selected portion of said monitor unit, a second alarm store connected with the malfunction detecting means and with said third register to cause said identifier code to be applied to said transmitting means, and second alarm counting means for causing said identifier code to be applied to said transmitting means a number of times equal to said predetermined number.

32. The invention as defined in claim 20 including a casing adapted to be mounted upon the body of said patient and being readily portable thereby, said sensing means being disposed externally of said casing, said converting means and digital data processor being disposed internally of said casing.

33. The invention as defined in claim 32 including mounting means connected with said casing and adapted to encircle a portion of the anatomy of said patient, said transmitting means being a radio transmitter including a radio transmitting antenna formed by a portion of said mounting means.

34. The invention as defined in claim 19 wherein said sensing means comprises a transducer for producing an electrical signal indicative of the occurrence of successive heartbeats.

35. The invention as defined in claim 34 wherein said transducer comprises at least two electrodes adapted to be electrically connected to the body of the patient.

36. The invention as defined in claim 19 wherein said transmitting means is a radio transmitter.

* * * * *